US010850060B2

(12) United States Patent
Searchfield et al.

(10) Patent No.: US 10,850,060 B2
(45) Date of Patent: Dec. 1, 2020

(54) TINNITUS TREATMENT SYSTEM AND METHOD

(71) Applicant: AUCKLAND UNISERVICES LIMITED, Auckland (NZ)

(72) Inventors: Grant Donald Searchfield, Auckland (NZ); Kei Kobayashi, Auckland (NZ); Samuel Irving, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 521 days.

(21) Appl. No.: 15/683,428

(22) Filed: Aug. 22, 2017

(65) Prior Publication Data

US 2018/0126115 A1    May 10, 2018

Related U.S. Application Data

(63) Continuation of application No. 13/501,050, filed as application No. PCT/NZ2010/000202 on Oct. 11, 2010, now Pat. No. 9,744,330.

(30) Foreign Application Priority Data

Oct. 9, 2009 (NZ) ....................... 580350

(51) Int. Cl.
*A61M 21/00* (2006.01)
*H04R 25/00* (2006.01)
(Continued)

(52) U.S. Cl.
CPC ............ *A61M 21/00* (2013.01); *H04R 25/75* (2013.01); *A61B 5/128* (2013.01);
(Continued)

(58) Field of Classification Search
CPC .......... A61M 21/00; A61M 2021/0027; H04R 25/75; H04R 25/552; H04S 1/002;
(Continued)

(56) References Cited

U.S. PATENT DOCUMENTS 4,759,070 A    7/1988  Voroba et al.
6,155,971 A    12/2000 Calhoun et al.
(Continued)

FOREIGN PATENT DOCUMENTS

CN    101263735 A    9/2008
CN    102647944 B    7/2016
(Continued)

OTHER PUBLICATIONS

"Head-Related Transfer Function and Virtual Hearing", Sun BOSUN, pp. 324, National Defense IndustryPress, Beijing.
(Continued)

*Primary Examiner* — Devin B Henson
(74) *Attorney, Agent, or Firm* — Joseph V. Saphia; Haug Partners LLP

(57) ABSTRACT

A tinnitus masking system for use by a person having tinnitus. The system comprises a sound delivery system having left and right ear-level audio delivery devices and is configured to deliver a masking sound to the person via the audio delivery devices such that the masking sound appears to originate from a virtual sound source location that substantially corresponds to the spatial location in 3D auditory space of the source of the tinnitus as perceived by the person. The masking sound being represented by left and right audio signals that are converted to audible sound by the respective audio delivery devices.

13 Claims, 20 Drawing Sheets

(51) Int. Cl.
  *H04S 1/00* (2006.01)
  *A61B 5/12* (2006.01)
  *H04S 7/00* (2006.01)
  *A61N 1/36* (2006.01)
(52) U.S. Cl.
  CPC ...... *A61M 2021/0027* (2013.01); *A61N 1/361* (2013.01); *H04R 25/552* (2013.01); *H04S 1/002* (2013.01); *H04S 7/302* (2013.01); *H04S 2420/01* (2013.01)
(58) Field of Classification Search
  CPC ..... H04S 7/302; H04S 2420/01; A61B 5/128; A61N 1/361
  See application file for complete search history.

(56) References Cited

U.S. PATENT DOCUMENTS

| | | | |
|---|---|---|---|
| 6,167,138 | A | 12/2000 | Shennib |
| 6,996,244 | B1 | 2/2006 | Slaney et al. |
| 7,327,848 | B2 * | 2/2008 | Squibbs .............. H04S 7/40 340/815.46 |
| 8,254,583 | B2 * | 8/2012 | Kim .............. H04S 3/00 381/1 |
| 2002/0177877 | A1 | 11/2002 | Choy |
| 2003/0044002 | A1 | 3/2003 | Yeager et al. |
| 2003/0114728 | A1 | 6/2003 | Choy |
| 2004/0131200 | A1 | 7/2004 | Davis |
| 2005/0018858 | A1 | 1/2005 | John |
| 2007/0093733 | A1 | 4/2007 | Choy |
| 2008/0132752 | A1 | 6/2008 | Choy |
| 2008/0226103 | A1 | 9/2008 | Schobben |
| 2009/0018466 | A1 | 1/2009 | Materna et al. |
| 2011/0046435 | A1 | 2/2011 | Jensen et al. |
| 2011/0054241 | A1 | 3/2011 | Jensen |

FOREIGN PATENT DOCUMENTS

| | | |
|---|---|---|
| CN | 105877914 B | 7/2019 |
| DE | 10128642 A | 1/2002 |
| DE | 102007046020 A | 4/2009 |
| EP | 3 184 046 B1 | 4/2010 |
| EP | 2 485 644 B1 | 8/2016 |
| WO | WO 2008/092663 A | 8/2000 |
| WO | WO 02/096154 A | 11/2002 |
| WO | WO 03/009639 A | 1/2003 |
| WO | WO 03/022001 A | 3/2003 |
| WO | WO 2004/098690 | 11/2004 |
| WO | WO 2006/136879 A | 12/2006 |
| WO | WO 2007/048017 A | 4/2007 |
| WO | WO 2009029040 A1 | 3/2009 |

OTHER PUBLICATIONS

Partial English Translation of the Office Action issued in corresponding Chinese Application No. 201080052680.1 dated Jul. 13, 2015.

Notification of the First Office Action from SIPO for corresponding Chinese application 201080052680.1 dated Jan. 22, 2014, English translation.

Notification of the Second Office Action from SIPO for corresponding Chinese application 201080052680.1 dated Nov. 15, 2014, English translation.

Communication pursuant to Article 94(3) EPC from European Patent Office for corresponding European application 10822295.1, dated Apr. 30, 2014.

Summons to attend oral proceedings pursuant to Rule 115(1) EPC for corresponding European application 10822295.1, dated Apr. 14, 2015.

Zhong, Xiaoli et al.: "Analysis on the spatial symmetry of head-related transfer function", ACTA Acustica, vol. 32, No. 2, Mar. 2007, pp. 13/39 to 20/39, in Chinese with English abstract.

Zotkin, Dmitry N. et al.: "Rendering Localized Spatial Audio in a Virtual Auditory Space", *IEEE Transactions on Multimedia*, vol. 6, No. 4, Aug. 2004.

Searchfield, G.D. et al: "Auditory Scene Analysis: Tinnitus What and Where.", International Tinnitus Seminar, Gothenburg, Sweden, Jun. 17, 2008.

Londero, Alain et al.: "Auditory and visual 3D virtual reality therapy for chronicsubjective tinnitus: theoretical framework", Virtual Reality, (2010), 14: (pages) 143-151.

Jastreboff, Pawl J.: "Phantom auditory perception (tinnitus): mechanisms of generation and perceition", *Neuroscience Research*, 8 (1990) pp. 221-254.

Extended European Search Report and Written Opinion issued by European Patent Office for corresponding European application 10822295 dated Jan. 30, 2013.

Partial translation of the first examination report dated Jul. 3, 2017 issued in corresponding Chinese application No. 201610391434.8.

Partial translation of the second examination report dated May 9, 2018 issued in corresponding Chinese application No. 201610391434.8.

Partial translation of the third examination report dated Jan. 14, 2019 issued in corresponding Chinese application No. 201610391434.8.

The extended European search report and written opinion, dated Feb. 23, 2017 issued in corresponding European application No. 16185168.8.

Notice of Allowance dated Nov. 4, 2019 issued in corresponding European application No. 16185168.8.

* cited by examiner

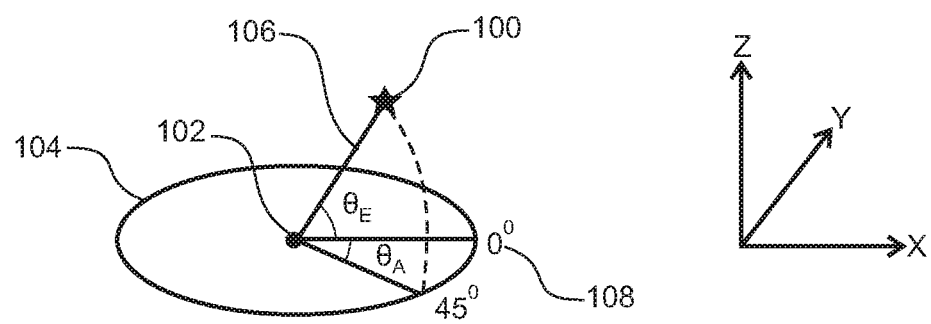
FIGURE 10A
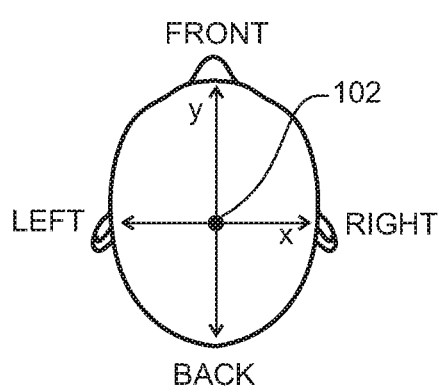 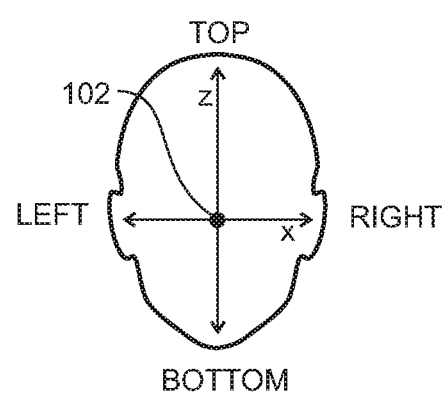
FIGURE 10B  FIGURE 10C

TINNITUS TREATMENT SYSTEM AND METHOD

CROSS-REFERENCE TO RELATED APPLICATIONS

This is a continuation of application Ser. No. 13/501,050, filed Jun. 28, 2012, which is a National Stage entry 35 U.S.C. § 371 of International Application No. PCT/NZ2010/000202 filed on Oct. 11, 2010, published on Apr. 14, 2011 under publication number WO 2011/0043678, which claims the benefit of priority under 35 U.S.C. § 119 of New Zealand Patent Application No. 580350 filed Oct. 9, 2009, the entire disclosure of which is incorporated herein by reference.

FIELD OF THE INVENTION

The present invention relates to the treatment of tinnitus. In particular, although not exclusively, the present invention is a tinnitus treatment system and method that may be employed by tinnitus sufferers to provide short-term and/or long-term relief.

BACKGROUND TO THE INVENTION

Tinnitus is the perception of sound in the absence of a corresponding external source. It can be perceived in one or both ears, or in the head, or outside the head. It is usually described as a ringing noise, but can also be in other forms such as hissing, buzzing, or roaring sounds. Tinnitus can be intermittent or it can be continuous and in such cases can be a cause of great distress to the sufferer.

Tinnitus is not a disease but a symptom resulting from a range of possible underlying causes including, for example, ear infections, foreign objects or wax in the ear, nose allergies, noise-related trauma, side effect of medication or other unexplained causes. Currently, there is no surgical cure for tinnitus. However, temporary relief for sufferers can be provided by external sound devices, for example masking instruments, as tinnitus sufferers often indicate that their tinnitus is less audible in the presence of sounds.

Typically, masking instruments use a noise generator to deliver a masking sound to the patient in order to mask the tinnitus. The masking instruments are often customised in that the frequency and intensity of the masking sound is often matched to the frequency and intensity of the tinnitus as perceived by the individual patient, and which can be assessed by an audiologist using various tests. Masking can be provided through ear-level or non-ear level sound generation devices including, for example, table top generators, bedside maskers, personal sound systems, standalone ear-level "maskers" for patients with normal hearing, and combination devices such as maskers integrated with hearing aids for the hearing impaired.

Another approach to tinnitus management, is the recent trend toward using Tinnitus Retraining Therapy (TRT). TRT is a specific clinical method based on a neurophysiological model of tinnitus. The method is aimed at habituation of reactions evoked by tinnitus, and subsequently habituation of the tinnitus perception. Typically, the therapy involves counseling, aimed at reclassification of tinnitus to a category of a neutral signal, and sound therapy, aimed at weakening tinnitus-related neuronal activity. Effectively the TRT method is trying to retrain the patient's brain so that they treat their tinnitus similar to natural sounds that they can accommodate.

It is an object of the present invention to provide an improved tinnitus treatment system and method, or to at least provide the public with a useful choice.

SUMMARY OF THE INVENTION

In a first aspect, the present invention broadly consists in a method of masking a person's tinnitus comprising: delivering a masking sound to the person via left and right ear-level audio delivery devices such that the masking sound appears to originate from a virtual sound source location that substantially corresponds to the spatial location in 3D auditory space of the source of the tinnitus as perceived by the person In a second aspect, the present invention broadly consists in a tinnitus masking system for use by a person suffering from tinnitus comprising: a sound delivery system having left and right ear-level audio delivery devices, the sound delivery system being configured to deliver a masking sound to the person via the audio delivery devices such that the masking sound appears to originate from a virtual sound source location that substantially corresponds to the spatial location in 3D auditory space of the source of the tinnitus as perceived by the person, the masking sound being represented by left and right audio signals that are converted to audible sound by the respective audio delivery devices.

Preferably, the ear-level audio delivery devices are headphones, earphones, hearing aids or the like.

Preferably, the sound delivery system further comprises an audio controller that is operable to control or trigger synchronized delivery of the left and right audio signals to the respective audio delivery devices.

Preferably, the masking sound is provided in the form of a digital audio file that is stored in memory in the audio controller for playback. Alternatively, the left and right audio signals of the masking sound are generated in real-time by a sound processor of the audio controller.

In one form, the audio controller is partially or completely integrated or onboard one or both of the audio delivery devices. In another form, the audio controller may be a separate external device that sends the left and right audio signals to the audio delivery devices via a wired connection or wireless communication.

In a third aspect, the present invention broadly consists in a method of determining a spatial property of tinnitus as perceived by a person comprising the steps of: sequentially presenting test sounds to the person from a series of virtual sound source locations in 3D auditory space; and receiving feedback from the person as to virtual sound source location that most closely corresponds to the spatial location in 3D auditory space of the source of the tinnitus as perceived by the person.

In a fourth aspect, the present invention broadly consists in a system for determining a spatial property of tinnitus as perceived by a person comprising: a sound generation system that is operable to present test sounds to the person from a series of virtual sound source locations in 3D auditory space; and a feedback system that is arranged to receive person feedback indicative of the virtual sound source location that most closely corresponds to the spatial location in 3D auditory space of the source of the tinnitus as perceived by the person and output spatial information indicative of the spatial location of the source of the tinnitus based on the person's feedback.

In one form, the sound generation system is configured to sequentially present test sound to the person from a range of different virtual sound source locations. In another form, the sound generation system is user operable to present the test sounds from user selected virtual sound source locations.

Preferably, the test sound has one or more sound attributes that substantially correspond or match one or more of the perceived sound attributes of the person's tinnitus. By way of example, the sound attributes may comprise any one or more of the following: pitch, frequency, bandwidth, temporal properties, intensity, loudness, or sound type.

Preferably, the test sounds are presented sequentially at different azimuth and elevation angles within respective predetermined azimuth and elevation ranges relative to a reference point in a 3D auditory space reference frame. Preferably, the reference point is the center of the midline axis between the ears.

Preferably, the azimuth is the angle of a vector about the reference point in a reference plane extending horizontally through the center of the person's head, and the elevation is the angle of the vector above or below the reference plane.

Preferably, the test sounds are continuously swept through the entire azimuth and elevation ranges. Alternatively, the test sounds may be sequentially presented at a series of discrete azimuth and elevation angles.

In a fifth aspect, the present invention broadly consists in a method of generating a spatial masking sound for a person having tinnitus comprising the steps of: receiving a masking sound, receiving spatial information indicative of the spatial location in 3D auditory space of the source of the tinnitus as perceived by the person; modifying the spatial playback properties of the masking sound based on the spatial information so as to generate a spatial masking sound that may be played to the person via left and right ear-level audio delivery devices such that the sound appears to originate from a virtual sound source location that substantially corresponds to the spatial location of the tinnitus as perceived by the person.

In a sixth aspect, the present invention broadly consists in a spatial masking sound generation system for a person having tinnitus comprising: a sound processor that is arranged to receive a masking sound and spatial information indicative of the spatial location in 3D auditory space of the source of the tinnitus as perceived by the person, and which is further configured to modify the spatial playback properties of the masking sound based on the spatial information so as to generate a spatial masking sound that may be played to a person via left and right ear-level audio delivery devices such that the sound appears to originate from a virtual sound source location that substantially corresponds to the spatial location of the source of the tinnitus as perceived by the person.

Preferably, the spatial masking sound is represented by left and right audio signals. More preferably, the spatial masking sound is stored or compiled into a digital audio file in any suitable audio format or other sound recording format, whether digital or analogue.

Preferably, the audio delivery devices are headphones, earphones, hearing aids, or any other suitable audio transducers for converting the audio signals into audible sound.

Preferably, the masking sound has sound attributes that are configured to substantially correspond to one or more of the sound attributes of the tinnitus as perceived by the person. By way of example, the sound attributes may comprise any one or more of the following: pitch, frequency, bandwidth, temporal properties, intensity, loudness, or sound type.

In a seventh aspect, the present invention broadly consists in a tinnitus masking audio system for a person having tinnitus comprising: left and right ear-level audio delivery devices that convert respective left and right audio input signals into audible sound, the left and right audio input signals representing a masking sound having a virtual sound source location in 3D auditory space that substantially corresponds to the spatial location of the source of the tinnitus as perceived by the person; and an audio controller that is operable to coordinate synchronized playback of the left and right audio signals over their respective audio delivery devices.

Preferably, the ear-level audio delivery devices are headphones, earphones, hearing aids or the like.

Preferably, the masking sound is provided in the form of a digital audio file that is stored in memory in the audio controller for playback. Alternatively, the left and right audio signals of the masking sound are generated in real-time by a sound processor of the audio controller.

In one form, the audio controller is partially or completely integrated or onboard one or both of the audio delivery devices. In another form, the audio controller may be a separate external device that sends the left and right audio signals to the audio delivery devices via a wired connection or wireless communication.

In an eighth aspect, the present invention broadly consists in a method of generating a personalised spatial masking sound for a person having tinnitus comprising:
    assessing one or more sound attributes of the tinnitus as perceived by the person;
    generating a masking sound having one or more sound attributes that substantially correspond to the perceived sound attributes of the person's tinnitus;
    assessing the location of the tinnitus sound source in 3D auditory space as perceived by the person; and
    modifying the spatial properties of the masking sound based on the assessed tinnitus sound source location so as to generate a spatial masking sound that may be played to the person via left and right ear-level audio delivery devices such that the sound appears to originate from a virtual sound source location that substantially corresponds to the spatial location of the source of the tinnitus as perceived by the person.

Preferably, the step of assessing one or more sound attributes of the tinnitus as perceived by the person comprises operating an assessment system to generate test sounds having configurable sound attributes for playback to the person, the assessment system being controlled by an operable graphical user interface. More preferably, this step further comprises receiving the person's feedback on the test sound that most closely corresponds to their perceived tinnitus for each sound attribute being assessed.

Additionally, or alternatively, the step of assessing one or more sound attributes of the tinnitus as perceived by the person comprises testing any one or more of the following: pitch-matching, loudness-matching, tinnitus specific measures, minimum masking level, residual inhibition, loudness growth and discomfort.

Preferably, the method further comprises the step of assessing the intensity of the tinnitus as perceived by the person at the location of the tinnitus sound source in 3D auditory space and further modifying the intensity of the masking sound based on the assessed intensity.

By way of example, the sound attributes may comprise any one or more of the following: pitch, frequency, bandwidth, temporal properties, intensity, loudness, or sound type.

Preferably, assessing the location of the tinnitus sound source in 3D auditory space as perceived by the person comprises sequentially presenting test sounds to the person from a range of virtual sound source locations in 3D auditory space; receiving feedback from the person as to virtual sound source location that most closely corresponds to the spatial location in 3D auditory space of the source of the tinnitus as perceived by the person. More preferably, the test sound is the masking sound.

Preferably, modifying the spatial properties of the masking sound comprises employing sound localization processing techniques and algorithms based any one or more of the following: ITD, ILD, and HRTFs.

The phrase "ear-level audio delivery device" as used in this specification and claims is intended to cover any type of audio delivery device that can be worn or located on, over or in a person's ear, whether a standalone audio component or integrated with another electronic device or system, and which can be driven to produce audible sound, including, by way of example only and not limited to, headphones, ear buds, and hearing aids.

The phrase "3D auditory space" as used in the specification and claims is intended to mean, unless the context suggests otherwise, the volume of space, whether external to a person or internal, from which actual or perceived sounds are determined as originating from according to the sound localisation processing of the person's brain.

The phrase "masking sound" as used in the specification and claims is intended to mean, unless the context suggests otherwise, any type of sound that can be used to mask (wholly or partially), cover or desensitize tinnitus as perceived by a person with the objective of relieving and/or desensitizing the person from the tinnitus sound over time and including for example, but not limited to, music, sound effects, background noise, white or broadband noise, or any combination of such sounds or other sounds suitable for this purpose.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

As used herein the term "and/or" means "and" or "or", or both.

As used herein "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIG. 10A is a schematic representation of the angular data used to characterise the spatial characteristics of the tinnitus sound source as perceived by the patient;

FIG. 10B is a midline cross-sectional top plan view of a patient's head and showing the X and Y axes of a 3D auditory space reference frame;

FIG. 10C is a midline cross-sectional elevation view of the patient's head of FIG. 10B and shows the X and Z axes of the 3D auditory space reference frame;

DETAILED DESCRIPTION OF PREFERRED EMBODIMENTS

Figure 1:
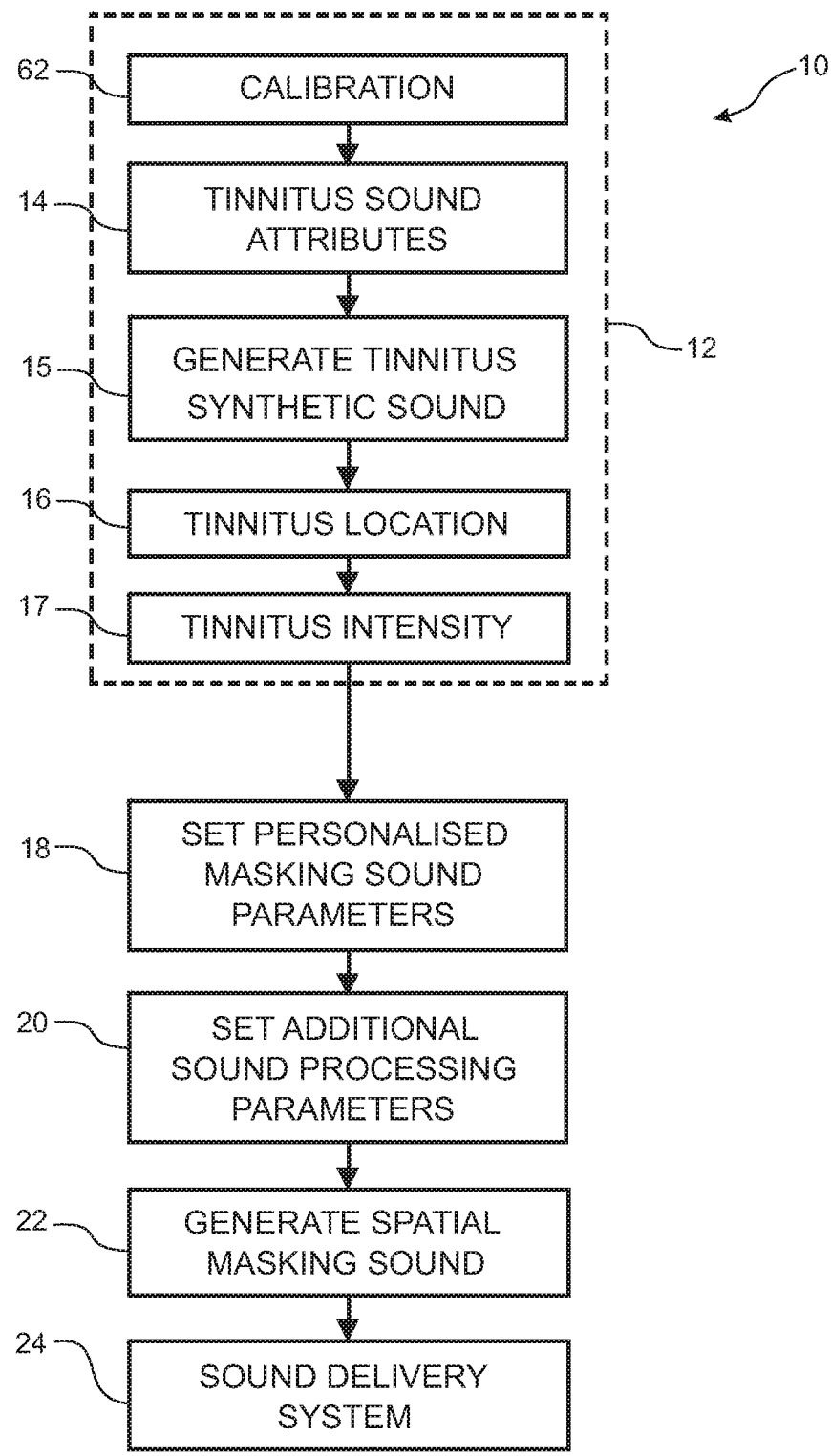
FIG. 1 is a flow diagram showing an overview of the steps in a method for generating a spatial masking sound for a patient suffering tinnitus in accordance with an embodiment of the invention.

1. Overview of Tinnitus Treatment Method and System

The invention relates to a tinnitus treatment system and method that is based on masking the tinnitus and/or desensitising the patient to the tinnitus. It has been identified that some of the distress associated with tinnitus is related to a violation of tinnitus perception from normal Auditory Scene Analysis (ASA). In particular, it has been identified that neural activity forming tinnitus is sufficiently different from normal sound activity that when formed into a whole image it conflicts with memory of true sounds. In other words, tinnitus does not localise to an external source. An inability to localise a sound source is "unnatural" and a violation of the fundamental perceptual process. Additionally, it has been identified that it is a lack of a context, or a lack of behaviourally relevant meaning, that force the brain too repeatedly or strongly attend to the tinnitus signal. For example, the sound of rain in the background is easily habituated to. The sound is associated with a visual and tactile perception or perceptual memory of rain as well. The context of the sound is understood so it can be processed and dismissed as unworthy of further attention. However, there is no such understanding of the tinnitus signal, which does not correspond to a true auditory object.

In some embodiments, the tinnitus treatment and system employs customised informational masking and desensitisation. Informational masking acts at a level of cognition and limits the brains capacity to process tinnitus, rather than "drowning it out", which is what some traditional white noise (energetic) maskers attempt.

The tinnitus treatment system and method presents a masking sound to the patient from a virtual sound source location in 3D auditory space that substantially corresponds to the spatial location of the source of the tinnitus as perceived by the patient. In some embodiments, the spatial 3D masking sound may also comprise other informational masking features, such as spectral, temporal, and/or intensity sound attributes that are matched to substantially correspond to the tinnitus sound as perceived by the patient. The system and method aims to enhance tinnitus masking by spatially overlapping the perceived tinnitus location and the spatial representation (or the virtual sound source location) of the masking sound.

As will be described in further detail later, the tinnitus treatment system and method employs virtual acoustic technology, such as a Virtual Acoustic Space (VAS) techniques or virtual surround sound processing, to present or deliver the masking sound to the patient so as to be perceived to originate or emanate from a predetermined direction and/or location in 3D auditory space, whether in the patient's head or external to the patient's head. Typically, the virtual acoustic technology can deliver a spatial masking sound via a pair of stereo (left and right) audio delivery devices such as, but not limited to, ear-level devices such as headphones, earplugs or hearing aids that are worn by the patient.

Referring to FIG. 1, an overview of an embodiment of the tinnitus treatment method 10 is shown. A preferred order of steps is shown by way of example only, but it will be appreciated that the order may be altered or varied in alternative forms of the treatment method. Additionally, some steps or stages may be omitted in other forms of the treatment method.

The first step 12 involves diagnosing the patient's tinnitus characteristics, as the spatial masking sound is customised for each patient. In this embodiment, the tinnitus diagnosis step 12 comprises five main stages. Firstly, a sound behavioural calibration diagnosis 62 is conducted to determine the patient's individual absolute hearing thresholds (audiogram) and uncomfortable loudness levels. Secondly, tinnitus sound attributes 14 are assessed. The tinnitus sound attributes assessed for the patient may comprise any one or more of the following: perceived sound characteristics (e.g., sound type, such as but not limited to pure tone, noise, environmental sounds, or any other sounds), bandwidth, temporal properties, loudness (intensity), and pitch. Such sound attributes or features can be assessed by an audiologist or clinician using various audio tests as will be explained in detail later. While not essential, it is desirable to assess the patient's perceived sound attributes of their tinnitus as in some embodiments the masking sound may be configured to match one or more of the sound attributes of the perceived tinnitus. For example, in the third stage, a tinnitus synthetic sound 15 matching one or more of the assessed sound attributes may be generated for use in the next assessment stages. This will not necessarily always be the case as in some embodiments unmodified masking sounds may be delivered to the patient, with the only characteristics overlapping being the spatial characteristics as explained next.

The fourth stage of the tinnitus diagnosis stage 12 involves assessing the spatial location 16 in 3D auditory space of the sound source location of the tinnitus as perceived by the patient. By way of example, the patient may perceive the tinnitus sound as originating from one ear, both ears, within their head or external to their head. Tests can be carried out by audiologist or clinician to determine the sound source location of the tinnitus as perceived by the patient, as will be explained in more detail later. The spatial location of the perceived tinnitus source may be represented in various forms in 3D auditory space, but in this embodiment the spatial location of the tinnitus is represented by a 3D direction vector that represents the direction from which the patient perceives their tinnitus as originating from relative to a reference point, such as the centre of their head or any other desired reference. In alternative forms, the 3D spatial location information may comprise both a 3D direction vector in 3D auditory space along with associated magnitude information representing the distance between the perceived tinnitus sound source location and the reference point. In some cases a predetermined distance to the perceived tinnitus source from the reference point (e.g. center of patient's head) will be assumed for the patient. This predetermined distance may be based on the sound localisation techniques or algorithms used.

The fifth stage of the tinnitus diagnosis stage 12 involves assessing the tinnitus intensity 17 in the spatial location in 3D auditory space. Tests can be carried out by audiologist or clinician to determine the intensity of the tinnitus as perceived by the patient as will be explained in detail later.

The tinnitus sound attribute information, spatial information, and tinnitus intensity information determined during the tinnitus diagnosis stage 12 is used as input for the following masking sound parameter setting steps 18 and 20. Firstly, a masking sound is selected and its sound parameters personalised 18 in view of the patient's tinnitus diagnosis results. The masking sound selected may, for example, be any sound recording or noise, such as music, white noise, environmental sounds, natural sounds, sound effects, or the like. One or more of the sound attributes for the masking sound may be configured to match the corresponding parameters of the tinnitus sound as perceived by the patient in the diagnosis step 14. Alternatively, the masking sound selected may be the synthetic sound generated at 15 in the tinnitus diagnosis step 14.

Various optional sound processing parameters 20 may then be configured, such as the masking sound play time, sound diffuse-field, and any desired playback intensity variation, such as ramping.

Once the desired masking sound parameters are set, the selected masking sound is signal processed at step 22 using virtual acoustic technology to generate a spatial masking sound that appears to originate in 3D auditory space from the same spatial location as the patient's perceived tinnitus source location. Additionally, sound processing may be employed to modify one or more of the masking sound attributes to match corresponding tinnitus sound attributes, depending on the desired personalisation settings from step 18.

The spatial masking sound output from step 22 may be in any suitable form for storage and playback, including any analogue storage medium or a digital sound file. In some embodiments, the spatial masking sound will be represented by a stereo audio signal and may be provided in various audio formats, whether analogue or digital, and including for example way or mp3 file formats. It will also be appreciated that the spatial masking sound may be stored on any suitable medium, whether analogue or digital, including on magnetic tapes, optical storage mediums such as CDs or DVDs, or readable memory devices, such as hard drives, memory sticks, whether standalone or part of another media, communication or entertainment device. As will be explained in more detail later, in preferred embodiments the spatial masking sound generation method is primarily employed for generating a masking sound for playback over hearing aids or headphones worn by the patient. In the context of hearing aids, these may have an onboard sound storage and/or generation system or may communicate with an external sound storage and/or generation system or device. In embodiments in which the sound generation system is onboard the audio delivery devices (e.g. hearing aids) or audio controller, the spatial masking sound output format may be configured to suit the audio delivery device input signal requirements.

The final step 24 in the treatment method is the playback of the spatial masking sound to the patient via a sound delivery system. The sound delivery system may be operated to play the spatial masking sound to the patient in accordance with a treatment plan. For example, the patient may be instructed to play the spatial masking sound at particular times during the day or when the tinnitus is most distressing and there may be customised treatment plans developed for each patient depending on their requirements and tinnitus distress profile.

In some embodiments, the spatial masking sound is provided in the form of a stereo audio signal that can be delivered or presented to the patient via left and right audio delivery devices, such as headphones or hearing aids at the ear level.

The stereo audio signal may be delivered to the audio delivery devices via any suitable type of audio control device having sound processing and playback capabilities, including for example a personal computer, PDA, cell phone, or portable audio player (e.g. iPod or mp3 player). Alternatively, the audio delivery devices and audio control device that stores and controls playback of the spatial masking system may be a standalone integrated treatment device or the audio control device may be integrated into hearing aids or the like.

2. An Example Embodiment of the Tinnitus Treatment Method and System

Figure 2:
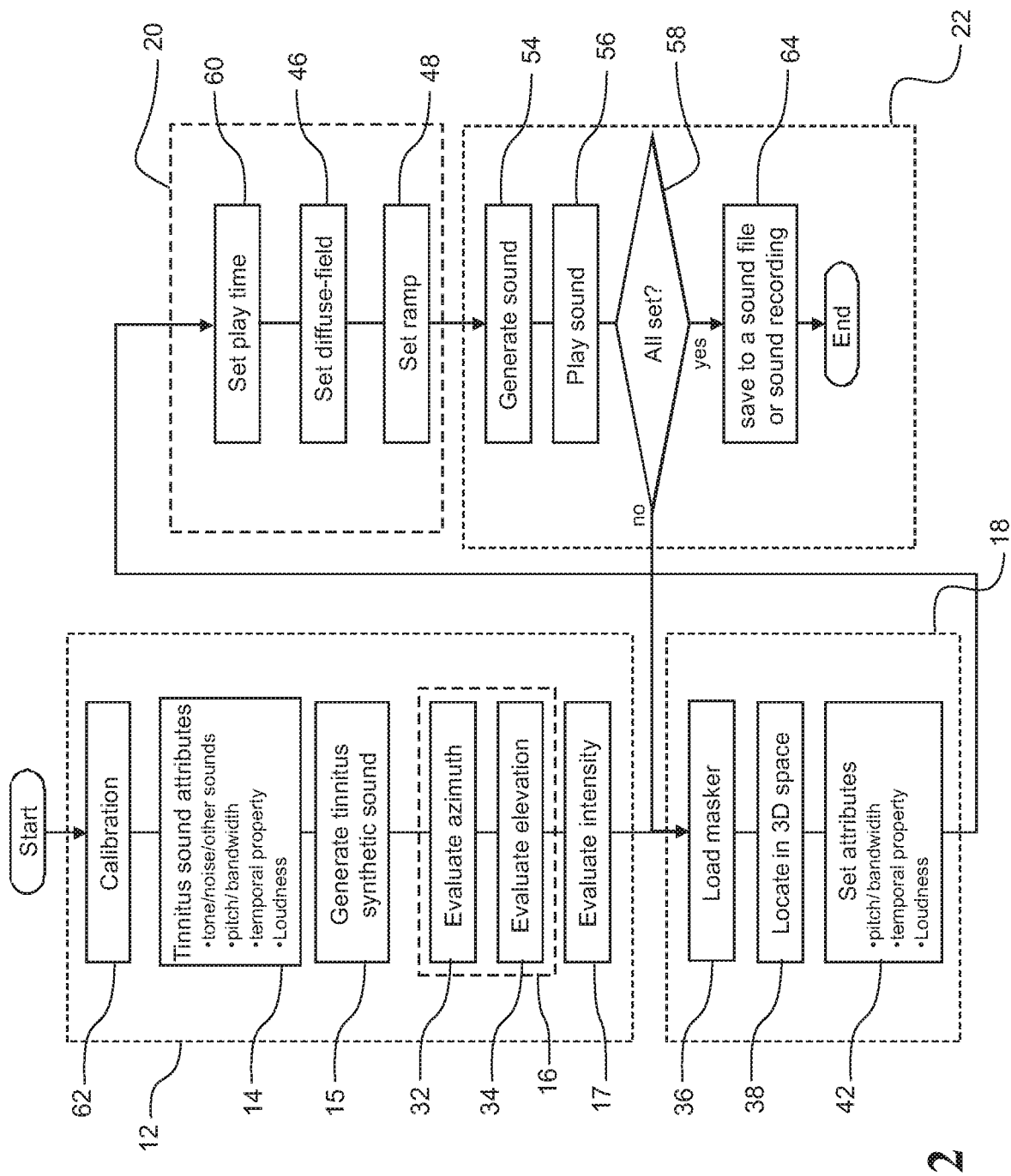
FIG. 2 is a flow diagram showing a more detailed breakdown of the steps in FIG. 1 in accordance with an embodiment of the invention.

Referring to FIG. 2, an example embodiment of the tinnitus treatment method will be explained in more detail with reference to the overview previously provided.

Assessment Tools for Tinnitus Diagnosis

The following tinnitus diagnosis 12 assessments in the treatment method may be performed using conventional audiology assessment techniques and systems for generating a profile of the sound attributes of an individual's tinnitus and conventional methods of storing or recording such information, whether electronically or otherwise. Additionally or alternatively, one or more of the tinnitus diagnosis assessments may be performed using a customised electronic tinnitus diagnosis system in the form of software running on a host computer system, which may be a Personal Computer having a processor, memory, data storage, user interface, display, and audio output interface for driving speakers, headphones, hearing aids or other connectable audio delivery devices for delivering test sounds generated by the assessment interfaces to the patient being assessed.

As will be explained further by way of example below, the tinnitus diagnosis system software may comprise one or more assessment interfaces or functions to assist the audiologist or clinician in profiling a patient's subjective tinnitus experience in terms of information relating to any of the sound attributes 14, 3D spatial location 16, and tinnitus intensity 17. Each of the assessment interfaces comprises an operable graphical user interface (GUI) that may be operated by the clinician and/or patient for assessing one or more sound attributes of the patient's tinnitus. The workflow of some of the assessment interfaces may be automated or semi-automated, or alternatively under complete control of the operator. The assessment information obtained by the use of each assessment interface may be stored electronically into a computer file or files that contain the information representing the patient's subjective tinnitus characterisation. The various assessment interfaces may interact with each other, such that assessment information from one interface is fed into one or more of the other interfaces. Optionally, the order of operation of the various interfaces may also be controlled, such that the tinnitus assessment for each patient follows a step-by-step protocol to accurately characterise the patient's tinnitus. The system may be operated by a clinician with the patient wearing the audio delivery devices for the test sounds, or may alternatively be operated by the patient as a self-assessment tool. As will be described with reference to FIGS. 3-9, 11 and 12, the overall GUI for the tinnitus diagnosis system may provide each assessment interface in a separate accessible tab, which when selected displays the operable GUI for that assessment interface.

By way of example, in one embodiment the tinnitus diagnosis system the sound format used may be 16-bit with a 44100 sampling rate. Monaural sound may be used to generate the stereo spatial sound. The system may support any sound format, including but not limited to the following formats: .wav, .mp3, .wma, .pcm.

Calibration

Firstly, a patient calibration assessment 62 may be carried out in the form of a behavioural calibration to determine the patient's absolute hearing thresholds and uncomfortable loudness levels (audiogram). This calibration assessment will be conducted using the audio delivery devices that will be worn by the patient, for example headphones or hearing aids. Such information may be determined from a patient's clinical audiogram in some embodiments. In some embodiments, the calibration of absolute hearing thresholds will be applied to compensate hearing at further stages and therefore the further loudness will be controlled with sound level (dB SL) upon the thresholds.

Figure 3:
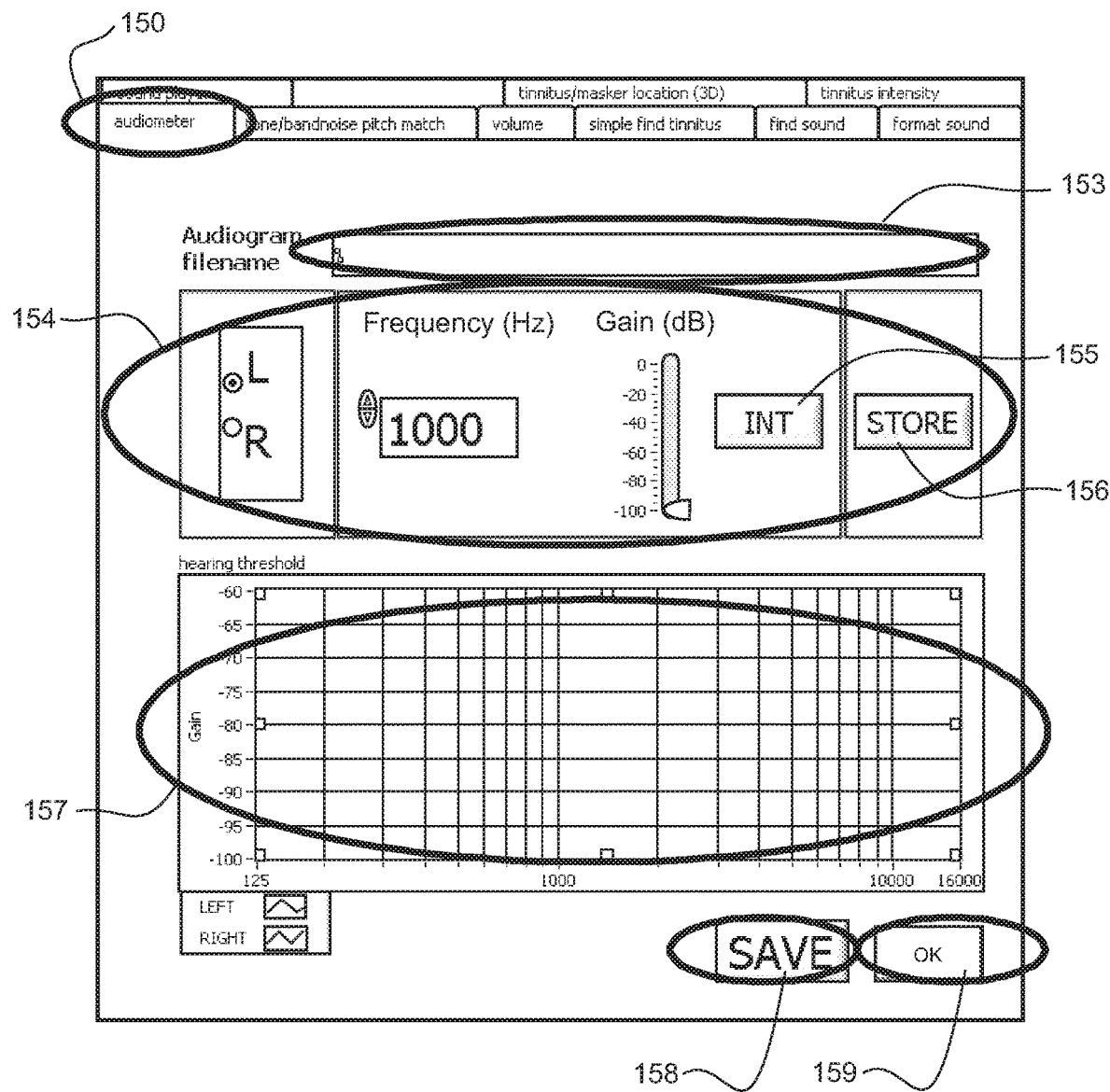
FIG. 3 shows a screen shot of the graphical user interface of an audiometer assessment interface of a tinnitus diagnosis system for use in calibration in accordance with an embodiment of the invention.

Referring to FIG. 3, in one embodiment of the method the calibration assessment may be performed using the audiometer assessment interface 150 of the tinnitus diagnosis system. In operation, the audiometer assessment interface provides a measurement tool for hearing thresholds for a range of frequencies. By way of example, the measurable frequencies may be 125 Hz, 250 Hz, 500 Hz, 750 Hz, 1000 Hz, 1500 Hz, 2000 Hz, 3000 Hz, 4000 Hz, 5000 Hz, 6000 Hz, 7000 Hz, 8000 Hz, 9000 Hz, 10000 Hz, 11000 Hz, 12000 Hz, 13000 Hz, 14000 Hz, 15000 Hz and 16000 Hz, although it will be appreciated that these frequencies may be altered as desired.

For a new test, the filename for storing the audiogram information may be entered into the filename box 153. Then, the main control panel 154 may be operated to sequentially generate test sounds at a desired frequency and gain for either the left or right. The initiate button 155 initiates the playback of the selected test sound to the patient, and the store button 156 saves the threshold result for that test sound frequency upon the patient's feedback. After each frequency is tested and stored, the audiogram results are plotted in the graphical display 157. The save button 158 may be operated to store all threshold results into the desired file entered into 153.

Alternatively, a previous audiogram performed by the patient on the system may be loaded by entering the relevant filename into box 153 and then operating the OK button 159 to load the previous results, which may then be updated for all or a selection of frequencies.

Tinnitus Sound Attributes

The treatment method then involves determining the patient's perceived tinnitus sound attributes 14, i.e. characterising the patient's tinnitus. In this example, the bandwidth, temporal properties, loudness, and pitch characteristics of the tinnitus as perceived by the patient are tested and recorded by an audiologist or clinician. As is known to those skilled in audiology, such tests typically present a series of sounds with varying attributes and seeking the patient's feedback in relation to the attributes that most closely match the sound attributes of the tinnitus as they perceive it. By way of example, such audiologist techniques that may be employed include pitch-matching and loudness-matching. Tinnitus specific measures to see how the patient's tinnitus compares with other environmental sounds may also be undertaken to find a tinnitus sound match.

Figure 4:
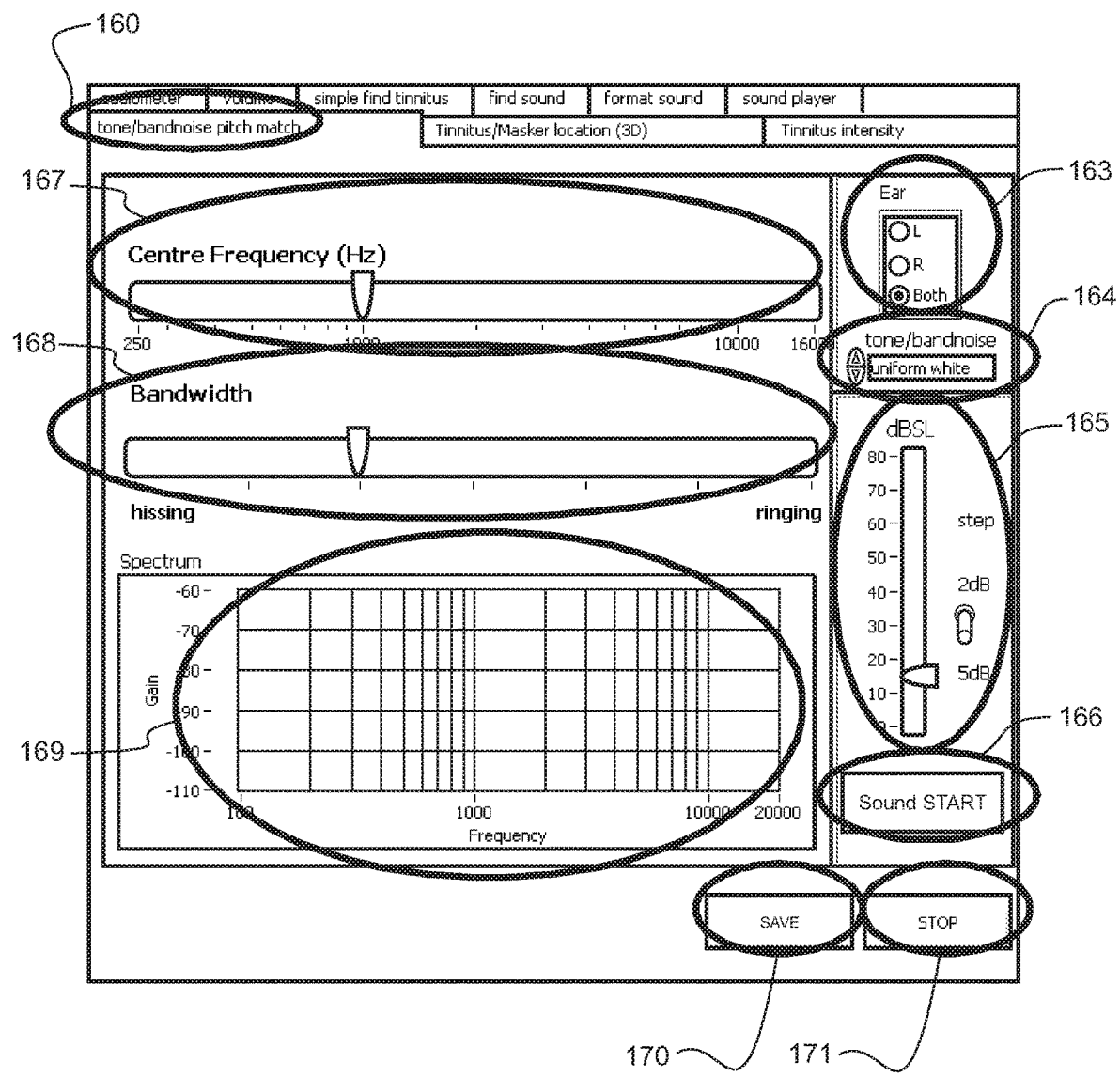
FIG. 4 shows a screen shot of the graphical user interface of a tone/bandnoise pitch match function interface of the tinnitus diagnosis system in accordance with an embodiment of the invention.

Referring to FIG. 4, in one embodiment of the method the pitch matching assessment may be performed using the tone/bandnoise pitch match function interface 160 of the tinnitus diagnosis system. The function uses tonal or band-noise stimuli with a 2AFC (2-alternative forced-choice) method to determine tinnitus pitch-match. It allows for modification of various parameters such as bandwidth and center frequency to promote a close match to the tinnitus percept. Test ear selection panel 163 may be operated to select either the left, right or both ears to test. The stimuli selection panel 164 may be operated to select the type of stimulus for the test sound playback, for example uniform white (white noise) or sine (tonal). The intensity slider scale 165 may be adjusted to set the desired intensity of the test sound. Operation of the start button 166 initiates the test sounds for playback to the patient for their feedback on pitch-matching to their tinnitus. Depending on their feedback, the center frequency 167 and/or bandwidth 168 of the stimuli may be adjusted to generate new test sounds to enable a closer pitch-match. The process is repeated until the closest pitch-match is obtained. The sound spectrum of the test sounds is displayed in the spectrum graphical display 169. The save button 170 may be operated to store the pitch-match results into a new or selected data file. A further stop button 171 is also provided for halting the interface. The interface compensates for any hearing loss as determined in the audiometer assessment interface 150.

Figure 5:
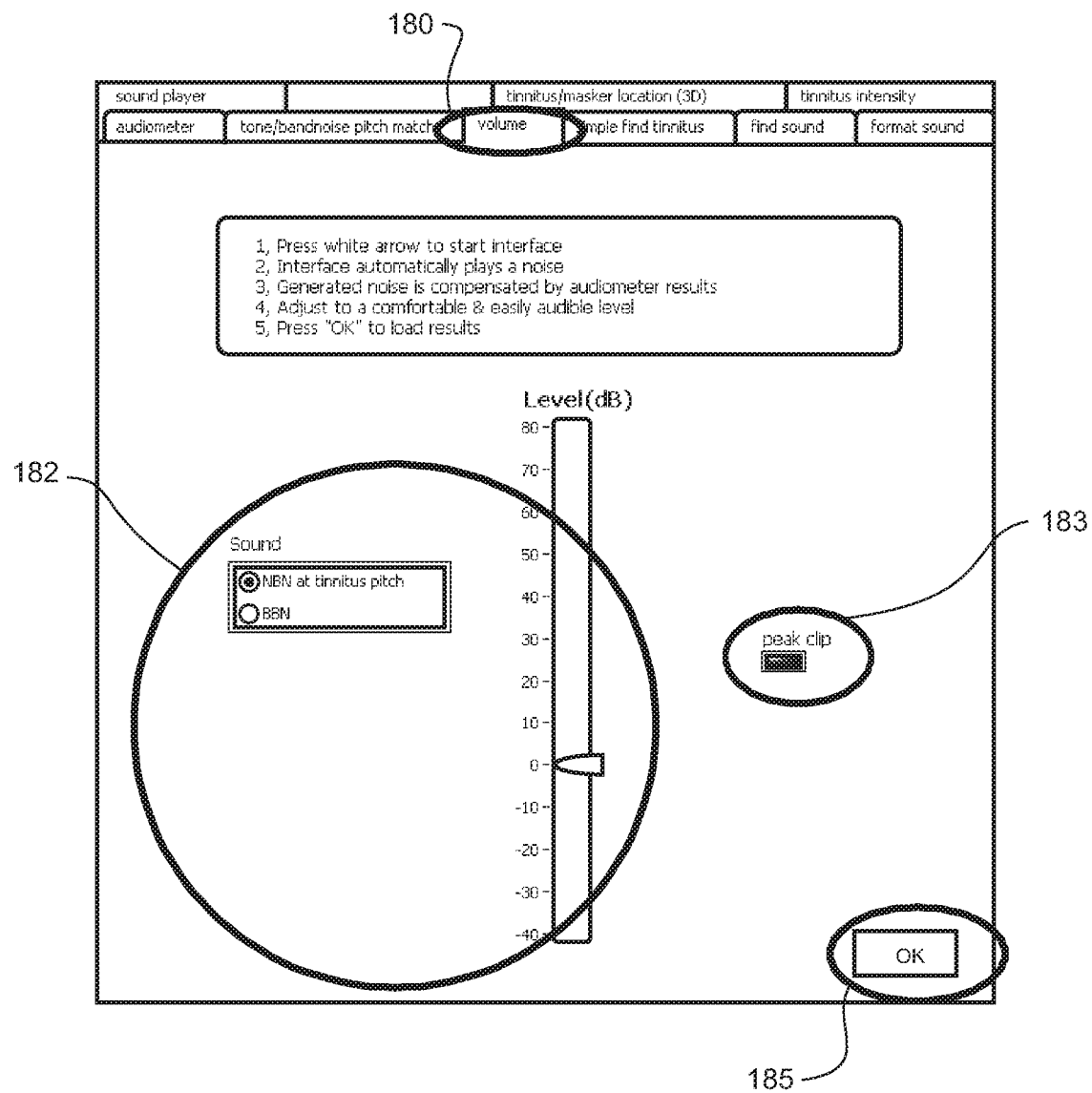
FIG. 5 shows a screen shot of the graphical user interface of a volume function interface of the tinnitus diagnosis system in accordance with an embodiment of the invention.

Referring to FIG. 5, in one embodiment of the method the loudness matching assessment may be performed using the volume function interface 180 of the tinnitus diagnosis system. Upon initialisation, the interface automatically plays a noise to the patient. The generated noise is compensated for any hearing loss based on the audiometer assessment interface 150 results. The user may then operate the main control panel 182 to adjust the volume slider scale to adjust the volume of the noise to a comfortable and easily audible level. Additionally, the type of sound may be selected between NBN (narrowband noise) at tinnitus pitch or BBN (broadband noise). By way of example, NBN at tinnitus pitch supplies more gain without peak-clipping, especially in the case of steeply-sloping, high-frequency hearing loss. A peak clip indicator 183 is provided if the adjusted volume via the slider scale is likely to introduce peak-clipping. A halt button 184 is provided to halt the interface. The OK button 185 may be operated to store the user-adjusted volume setting in a data file, which may then be used by subsequent interfaces.

Figure 6:
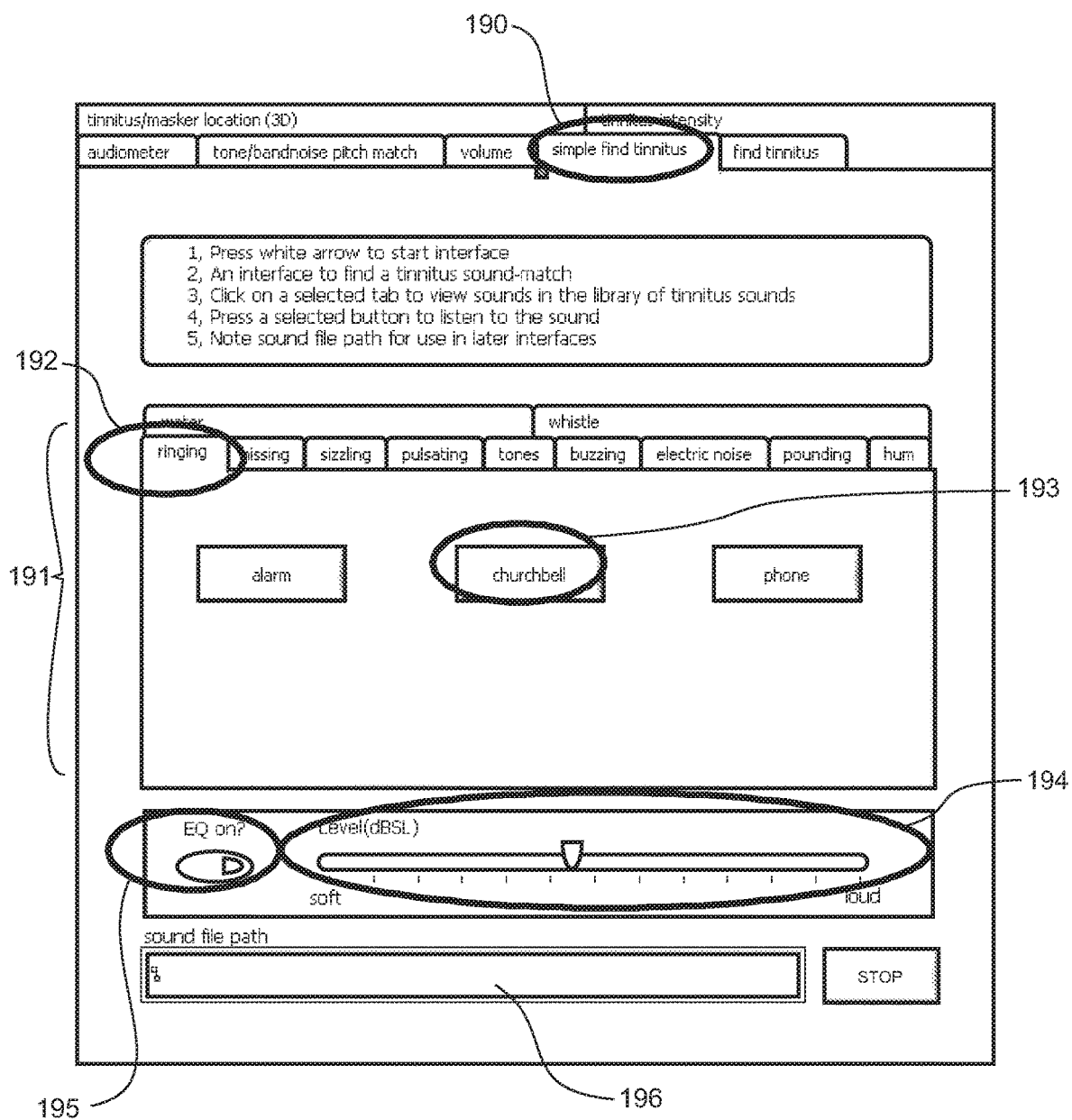
FIG. 6 shows a screen shot of the graphical user interface of a first tinnitus sound-match function interface of the tinnitus diagnosis system in accordance with an embodiment of the invention.

Referring to FIG. 6, in one embodiment of the method a tinnitus sound matching assessment may be performed using a first tinnitus sound-match function interface 190 of the tinnitus diagnosis system. The purpose of this interface is to allow a patient to characterise their subjective tinnitus percept via a sound library to help identify a tinnitus sound-match from environmental sounds. The audiologist or clinician may ask the patient to describe their tinnitus and then proceed to play any suitably matching sounds to the patient for their feedback on matching. It will be appreciated that the interface itself may alternatively be configured to guide the patient through this process automatically as a self-assessment tool if desired. A main sound library panel is provided at 191 comprising sound category tabs 192, and for each category one or more sound buttons 193 that are operable to playback a sound of the type indicated on the button for the patient's feedback for matching to their tinnitus. A volume/intensity presentation level slider scale 194 is provided for adjusting the presentation volume of the test sounds. The default volume level is automatically set according to the audiometric threshold values obtained by the audiometer interface 150. The volume level may be adjusted to be softer or louder using the scale 194 depending on the patient's subjective tinnitus impressions. An equaliser button 195 may be operated to adjust the sound frequency components of the test sounds to improve sound quality if needed. The sound file path in the sound library of the selected sound button may be displayed to the user at 196. The sound library of different types of sound files may be located locally in data storage on the host computer system or an accessible external storage database. The closest environmental sound match may then be recorded for the patient or stored in a data file associated with the patient.

Figure 7:
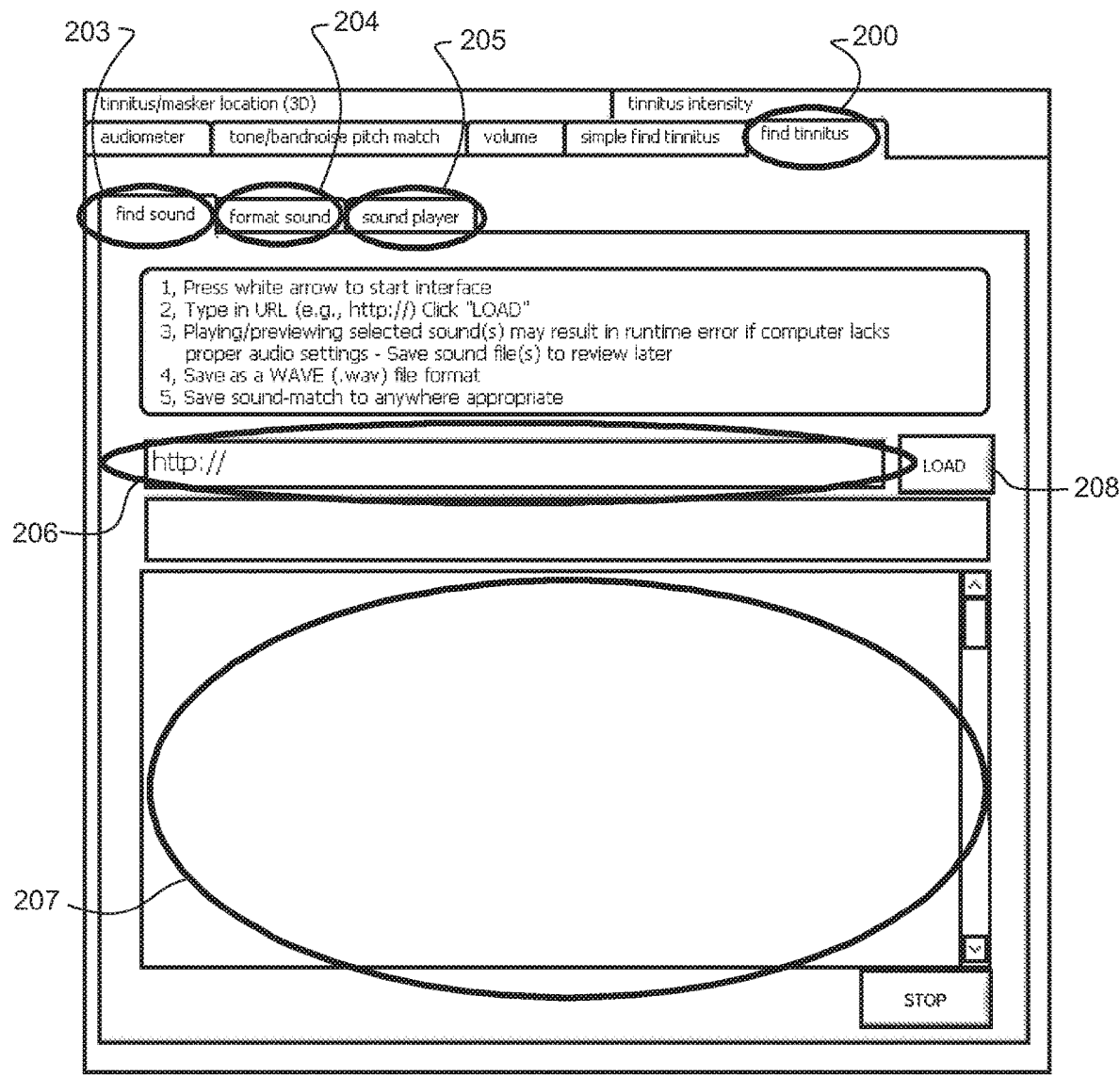
FIG. 7 shows a screen shot of the graphical user interface of a find sound search feature of a second tinnitus sound-match function interface of the tinnitus diagnosis system in accordance with an embodiment of the invention.
Figure 8:
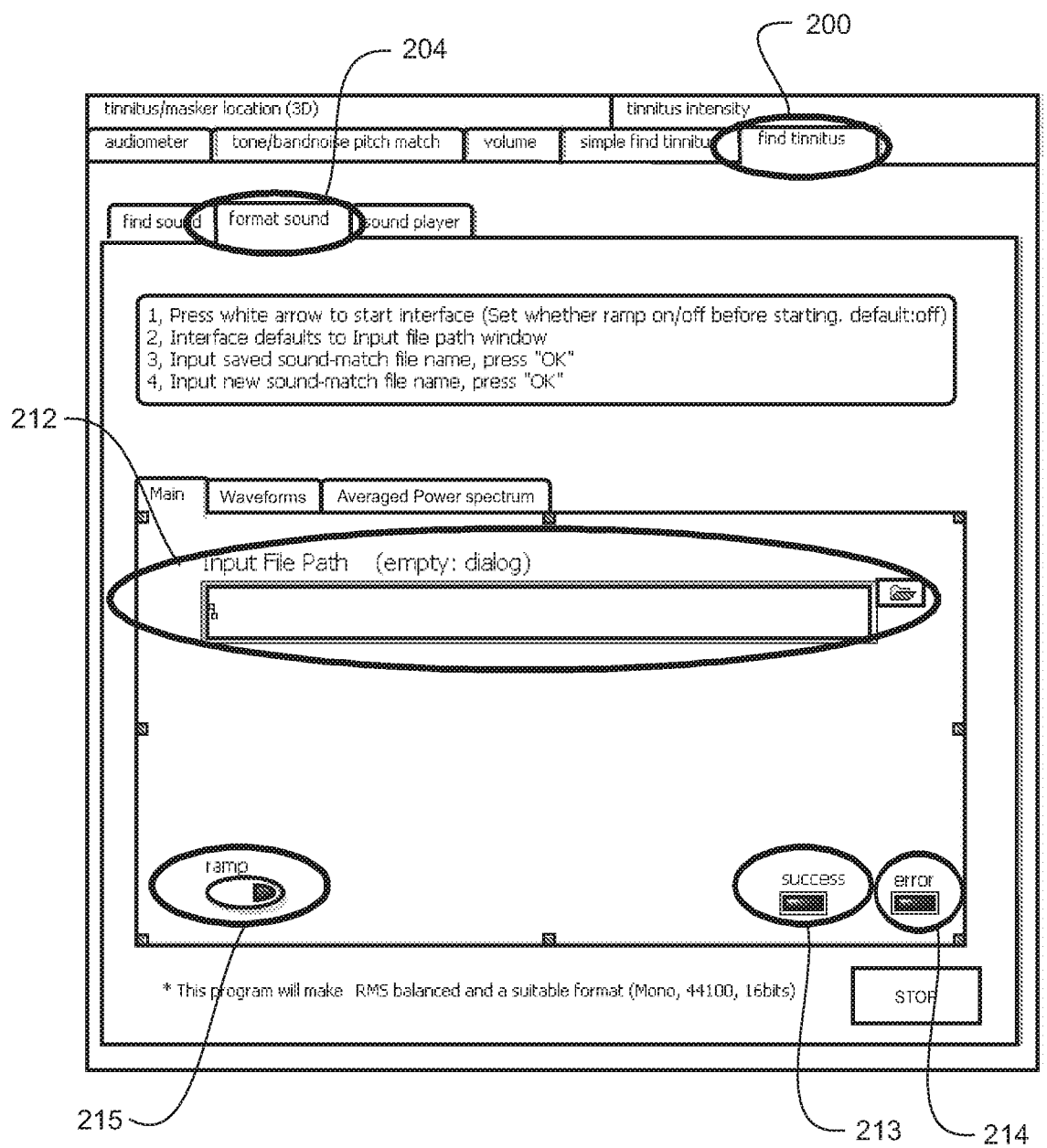
FIG. 8 shows a screen shot of the graphical user interface of a format sound search feature of the second tinnitus sound-match function interface of the tinnitus diagnosis system in accordance with an embodiment of the invention.
Figure 9:
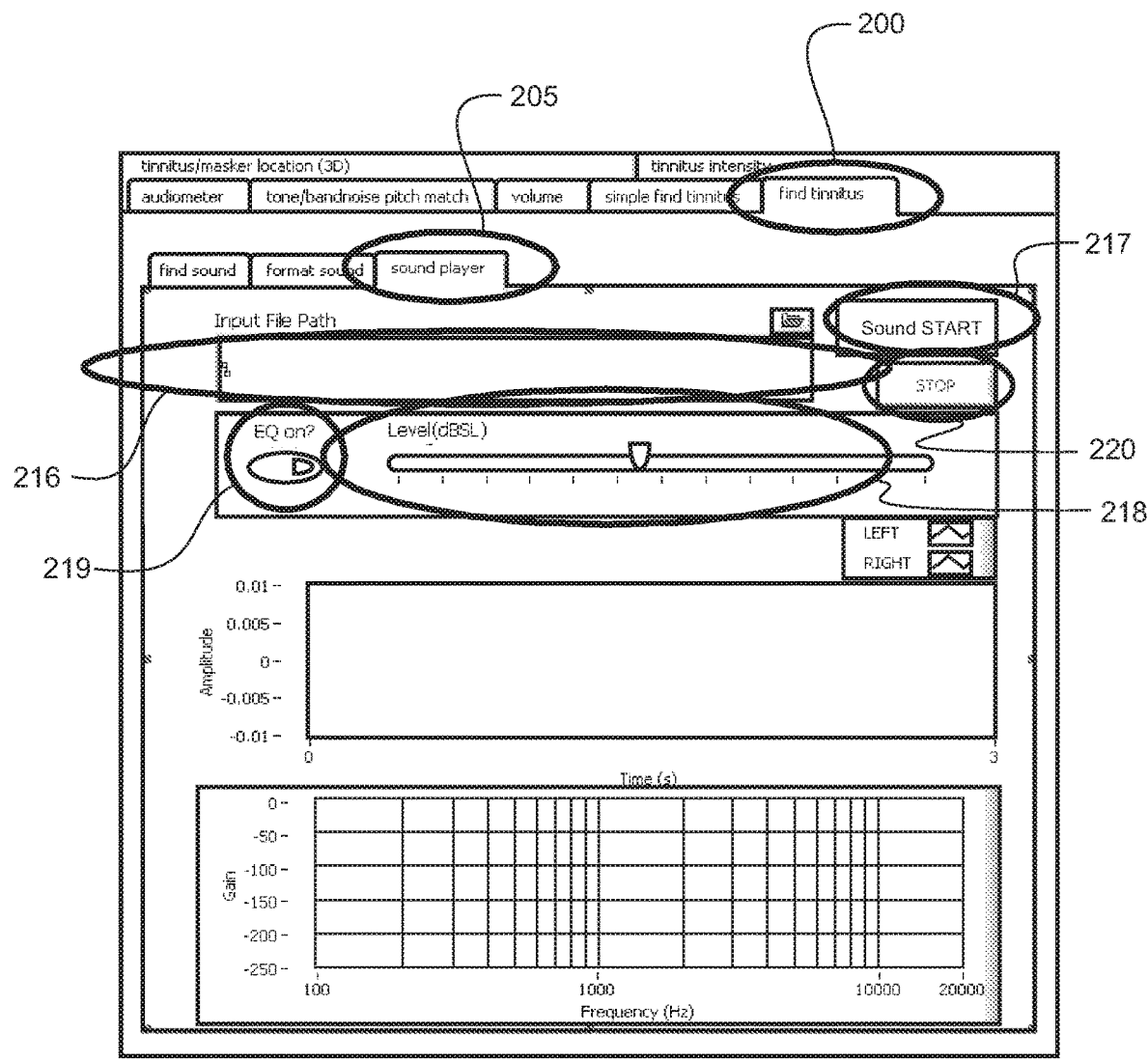
FIG. 9 shows a screen shot of the graphical user interface of a sound player feature of the second tinnitus sound-match function interface of the tinnitus diagnosis system in accordance with an embodiment of the invention.

Referring to FIGS. 7-9, in one embodiment of the method a tinnitus sound matching assessment may be performed using a second tinnitus sound-match function interface 200 of the tinnitus diagnosis system. This second interface 200 may be used as an alternative to the first interface 190 if the patient requires a larger sound library of environmental sounds from which to assess a tinnitus sound match. In this embodiment, the interface 200 has three main sub-interfaces, namely a find sound interface 203, a format sound interface 204, and a sound player interface 205.

Referring to FIG. 7, the find sound sub-interface 203 offers a search interface for searching the Internet for environmental sounds for playback. A website search interface may be loaded by entering a website address into the URL bar 206. The website may be loaded into search panel 207 upon operation of the load button 208. The website address may for example be a sound search interface for searching the internet, an intranet or other database for sound files that match one or more descriptive keywords and/or sound file parameters or a sound generation website. The sound files located may then be played to the patient to find the closest match to their tinnitus. The closest tinnitus-sound match files may also then be downloaded and stored from the sound file links.

Referring to FIG. 8, the format sound sub-interface 204 is configured to convert any downloaded sound file from the find sound sub-interface 203 as selected in the file path interface 212 into a suitable format for use in the tinnitus diagnosis system. For example, the format sound sub-interface may be configured to convert a sound file into monoaural, 16-bit with a 44100 sampling rate, or any other desired sound format and store the formatted sound file. Success 213 and error 214 indicators are provided to indicate whether the selected file has been successfully formatted or not. A ramp button 215 is also operable to apply a ramp function to the sound files to remove any audible pops, clicks or distortion, if necessary.

Referring to FIG. 9, the sound player sub-interface 205 is configured as an audio tool for playing back a preview of the sound found via the find sound sub-interface 203, and which the patient perceives as characterising or describing their tinnitus percept. The sound file to be previewed may be selected using the file selection panel 216 and the sound may be played to the patient or user by operation of the sound start button 217. A volume adjustment is available via operation of slider scale 218 to make the presentation softer or louder. The interface is configured to initially default to a presentation level that corresponds to the threshold values assessed in the audiometer interface 205. An operable equaliser button 219 is also provided for adjusting the sound frequency components to improve sound quality, if needed. A stop button 220 is provided to halt playback.

Generation of Tinnitus Synthetic Sound

Reverting to FIG. 2, after one or more of the assessments 62,14 have been conducted, whether via the tinnitus diagnosis system interfaces or otherwise, the clinician generates a tinnitus synthetic sound 15 that most closely matches at least one, but preferably all, sound attributes of the tinnitus as perceived by the patient based on the information obtained during the assessments. If the tinnitus diagnosis system is used, all the assessment information from the interfaces may be stored in one or more accessible data files associated with the patient and which profile the characterisation of their tinnitus. For example, the synthetic sound 15 generated may be a tone, noise, or environmental sound that is further signal processed to match the patient's characterisation of their tinnitus in terms of bandwidth, temporal properties, loudness (intensity), and pitch, or any other assessed sound attributes. This synthetic sound 15 may be utilised as the test sound in the next tinnitus spatial information assessment step 16.

Tinnitus Location

The next step 16 involves the clinician assessing the spatial information corresponding to the tinnitus as perceived by the patient. In this embodiment, the clinician determines the 3D direction vector in 3D auditory space from which the tinnitus sound appears to originate as perceived by the patient. In this embodiment, the 3D direction vector is represented angularly by azimuth angle $\theta_A$ and elevation angle $\theta_E$ relative to a reference point or frame. It will be appreciated that the spatial information relating to the perceived tinnitus sound source direction or location may be represented in any other suitable form of coordinate system if desired. In addition, it will be appreciated that the spatial information may comprise a 3D direction vector and magnitude to the perceived sound source location so that distance as well as direction to the location can be used when generating the spatial masking sound.

Referring to FIG. 10A, an example of the 3D direction vector 106 to perceived tinnitus source location 100 is shown. In this example, the reference point 102 represents the centre of a patient's head and the circular reference plane 104 is located parallel to the transverse plane of the human anatomy i.e. it extends horizontally from the back of the head to the front of the head when upright. In one form, the reference point may be the center of the midline axis between the patient's left and right ears. The 3D direction vector 106 to the perceived tinnitus source location is represented by azimuth angle $\theta_A$ representing the azimuth angle of the 3D direction vector 106 relative to reference vector 108 in the circular reference plane 104 and elevation angle $\theta_E$ representing the angular elevation of the 3D direction vector 106 relative to the circular reference plane 104, which may be above or below the plane between 90 and −90°. The azimuth angle $\theta_A$ may be anywhere between 0-359°.

As will be explained in more detail later, the sound generation system employs virtual acoustic technology to generate the test sound to appear to originate from a direction in 3D auditory space that corresponds to the azimuth and elevation desired.

In one embodiment, the sound generation system is configured to sequentially generate a series of spatial sounds that are presented to originate through an azimuth angle of between 0-359° (elevation angle=0°) in the circular reference plane 104 in order to match to the tinnitus azimuth. As the series of test sounds (for example the tinnitus synthetic sound 30) are sequentially played through the azimuth range, feedback is received from the patient as to the test sound that most closely corresponds to the spatial location or direction from which their tinnitus is perceived as originating from. Once the tinnitus azimuth is located, spatial sounds at that specific azimuth are presented to originate through an elevation range of between −90° to 90°, and feedback is received from the patient as to the elevation angle that most closely corresponds to the tinnitus source location as they perceive it. In one form, the test sounds may be swept continuously through the azimuth and elevation ranges. In another form, the test sounds may be sequentially presented at discrete equi-spaced azimuth and elevation angles in the ranges or alternatively at non-uniformly spaced azimuth and elevation angles in the ranges as desired.

It will be appreciated that other testing processes may alternatively be used to assess the tinnitus azimuth and elevation angles. For example, the elevation angle may be assessed prior to the azimuth angle if desired. A further alternative may involve presenting the test sounds through azimuth and elevation angle ranges concurrently, i.e. present the elevation range at each azimuth angle or vice versa. In addition to detecting the direction of the perceived tinnitus sound source, the intensity of the test sounds may be varied so as to enable assessment of the perceived distance of the tinnitus sound source location relative to the reference point.

Figure 11:
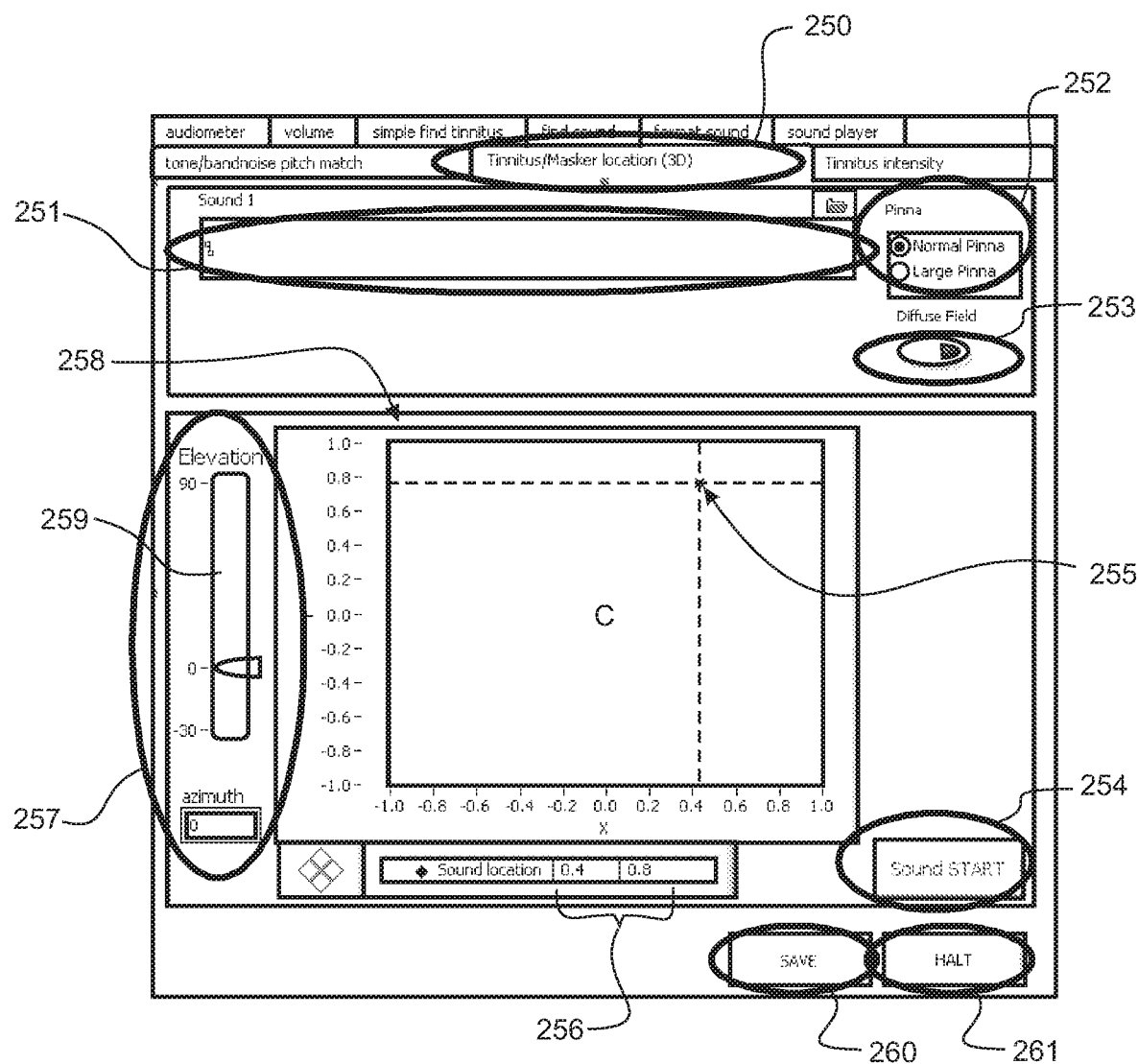
FIG. 11 shows a screen shot of the graphical user interface of a 3D spatial location function interface of the tinnitus diagnosis system in accordance with an embodiment of the invention.

In another embodiment, the sound generation system may be operable and controllable by the clinician or patient to manually vary the 3D spatial location (azimuth and elevation) of the test sound as desired to find a location match. By way of example only, the sound generation system may form part of the tinnitus diagnosis system. Referring to FIG. 11, a 3D spatial location interface function 250 of the tinnitus diagnosis system may be operable to present a test sound to the user such that it appears to originate from a desired 3D spatial location. The test sound file for playback at the desired location may be selected using file selection panel 251. The sound file may be the synthetic sound file generated at step 15 or any other desired test sound. The user may select the pinna size of the listener, for example normal pinna or large pinna using selection options 251,252 and this will configure the system to more accurately locate the test sound in virtual 3D space for the user using virtual acoustic technology. A diffuse field button 253 may be operated to clean the sound signal, depending on the type of test sound that has been selected. Operation of the start sound button 254 initiates playback of the test sound to the patient.

The interface 250 is configured to provide a display grid 258 that represents the spatial location 255 of the test sound presented in a reference frame relative to the center of the patient's head as shown at C. The Cartesian coordinates of the spatial location of the test sound are displayed at 256, and the elevation and azimuth displayed in interface 257. The clinician or patient may drag and drop the cursor 255 around the display grid of the GUI to alter the spatial location of the test sound presented so as to find the closest match to the tinnitus location as perceived by the patient. Each time the cursor is placed in a new position the spatial playback properties of the test sound are altered to correspond to the new location. In this embodiment, the display grid 258 represents the azimuth of the test sound location and the user may configure this first by locating the cursor 255 at a position on the grid that represents whether they perceive their tinnitus to be originating. By way of example, the top of the grid may represent the front of the head, the bottom of the grid the back of the head, and the left and right sides of the grid may represent the left and right sides of the head respectively. Once the azimuth of the perceived tinnitus location is determined, the user may then find the elevation of the perceived tinnitus location relative to the midline axis between their ears, i.e. whether the patient perceives their tinnitus to be originating in a plane located at the midline (0° elevation) or plane above or below the midline. To adjust the elevation, the user may use the slide scale 259 to adjust the elevation of the test sound presented. Once the user has located the test sound in a position that most closely matches their perceived tinnitus location, they may save this spatial information into a data file by operating the save button 260. A halt button 261 is also provided for halting the interface if desired.

The perceived tinnitus source location does not necessarily have to be represented in 3D auditory space by azimuth and elevation angles relative to a reference point. In another forms, the 3D auditory space may be represented by three-axis Cartesian coordinates (X, Y, Z) as shown in FIGS. 10B and 10C. For example, the origin of the 3-axis orthogonal reference frame may again be the center of the midline axis between the patient's ears and this midline axis may be the X-axis. The Y-axis is orthogonal to the X-axis and extends horizontally between the front and back of head, as shown in the display grid 258 of the 3D spatial location interface function 250 for example. The Z-axis is orthogonal to the X-Y plane and extends vertically between the top and bottom of the head. Based on this reference frame, the patient's perceived tinnitus location, such as a 3D direction vector, may be defined by 3-axis X,Y,Z coordinates. The X, Y, Z axes may extend external to the patient's head.

Tinnitus Intensity at 3D Location

Reverting to FIG. 2, the next stage 17 is evaluating one or more intensity levels for the test sound as perceived by the patient at the spatial location determined in the location assessment 16. The following levels may be determined: the threshold level (THL) at which the sound at the perceived tinnitus location can be detected, the minimum amount of intensity required for this sound to mask or cover the patient's tinnitus percept (MML—minimum masking level), and the amount of intensity perceived to be as loud as the patient's subjective tinnitus percept (LVL). Sensation level methods may be employed to determine the MML. Residual inhibition tests for determining the occurrence, following the presentation of a masking sound, of temporary (partial or complete) suppression of an individual's tinnitus may be carried out. Loudness growth and discomfort tests may be carried out in the form of a standardised measurement of loudness perception.

Figure 12:
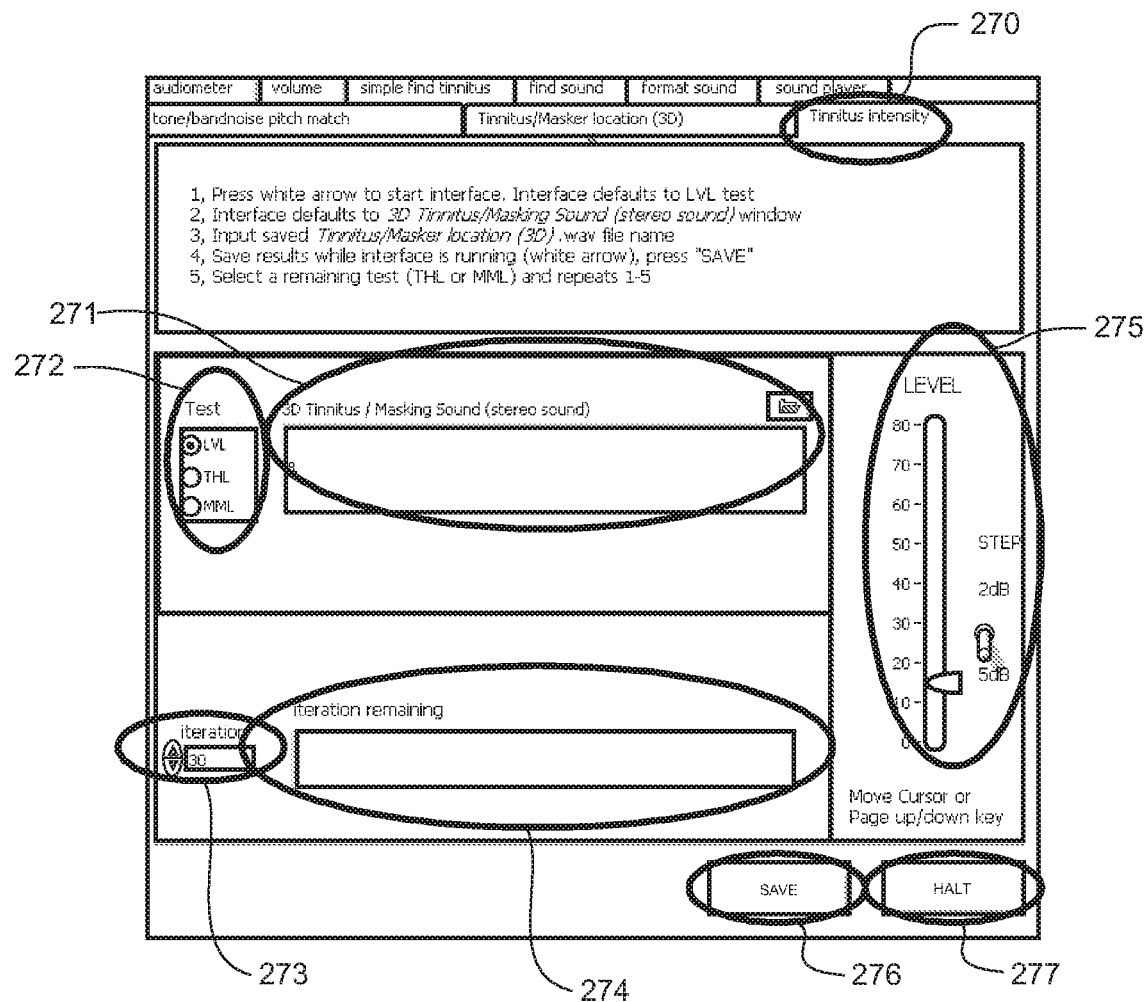
FIG. 12 shows a screen shot of the graphical user interface of a tinnitus intensity function interface of the tinnitus diagnosis system in accordance with an embodiment of the invention.

Referring to FIG. 12, in one embodiment, the tinnitus diagnosis system provides a tinnitus intensity assessment interface 270 that may be operated by a user to determine one or more of the intensity levels MML, THL, and LVL. The interface 270 is operable to present a test sound, such as the generated synthetic sound 15 or otherwise, at the spatial location corresponding to the patient's perceived tinnitus at various intensities for assessing the thresholds. The test sound file may be selected at file selection interface 271. The type of test or assessment being conducted, for example MML, THL or LVL, may be selected in panel 272. Playback of the sound file is initiated via the interface and may be repeated for a number of desired iterations as selected at 273 with the playback time remaining being displayed at 274. During playback, the user may adjust the volume slider scale 275 to adjust the intensity level to suit the level being assessed, i.e. MML, THL, LVL. Once the volume has been adjusted for each test level, the results or intensity level information are saved to a data file as triggered by operation of the save button 276. A halt button 277 is also provided to halt the interface at any point if desired.

Set Personalised Masking Sound Parameters

Once the tinnitus diagnosis stage 12 is complete, the sound attributes information, spatial information, and intensity level information relating to the tinnitus as perceived by the patient is used as input for the next step of setting the personalised masking sound parameters 18. As previously indicated, the assessment information may be stored in an accessible electronic data file or files, or recorded in any other suitable form. Firstly, a new masking sound may be created or a previous stored masking sound selected at step 36 for loading into the remainder of the process. If a previous masking sound is selected, then the sound parameters of that sound will be personalized for the patient in view of the information from the tinnitus diagnosis stage. If a new masking sound is to be created, then a stimulus will need to be selected from a masking sound library and the sound parameters of that stimulus personalised in view of the information from the tinnitus diagnosis stage. This library may include for example, but is not limited to, white noises, low frequency noises, fractal sounds, pseudo-random varying frequency tones (e.g. piano tones and the note), natural sounds (e.g. rain) or any other suitable therapy sounds. Alternatively, the tinnitus synthetic sound 15 generated in the tinnitus diagnosis stage 12 can be loaded for the next masking parameter setting stage 18.

The next step 38 in personalisation of the masking sound is locating the spatial position of the 3D spatial masking sound by selecting target azimuth and elevation angles. These angles are configured to correspond or match the tinnitus azimuth and elevation angles of the spatial information as assessed in the tinnitus diagnosis step.

The next steps 42 comprise modifying the selected stimulus of the new masking sound or the pre-stored masking sound by tuning various sound attribute parameters, such as the bandwidth, temporal property, loudness, and pitch. In some embodiments, one or more of the sound attributes may be tuned so as to substantially correspond to one more of the corresponding parameters of the perceived tinnitus as determined in the diagnosis step 12. As to loudness tuning, this can also be used to match the Minimum Masking Level (MML), Minimum Effective Masking Level (MEML) and Desired Masking Level (DML) of the spatial masking sound at the virtual 3D sound source location for the individual patient, and which may be assessed in the calibration phase 62. MML represents the minimum level of sound required to cover the tinnitus making it inaudible. MEML represents the minimum level of sound that the listener finds effective in reducing tinnitus audibility. DML represents the level of sound the listener prefers to use to mask their tinnitus.

Set Additional Sound Processing Parameters

After personalisation of the masking sound has been configured, additional optional sound processing parameters 20 may be configured. These steps may be optional depending on the spatial masking sound desired and the tinnitus treatment plan being employed by the patient. By way of example only, the play time 60 for the masking sound file may be set and the diffuse-field 46 for the spatial masking sound may be configured to match a desired profile. For example, the diffuse-field may be configured such that the flow of sound energy is substantially equal in all directions from the virtual 3D tinnitus source location or alternatively the diffuse-field may be configured to focus the sound energy in one or more particular directions or regions.

Figure 13A:
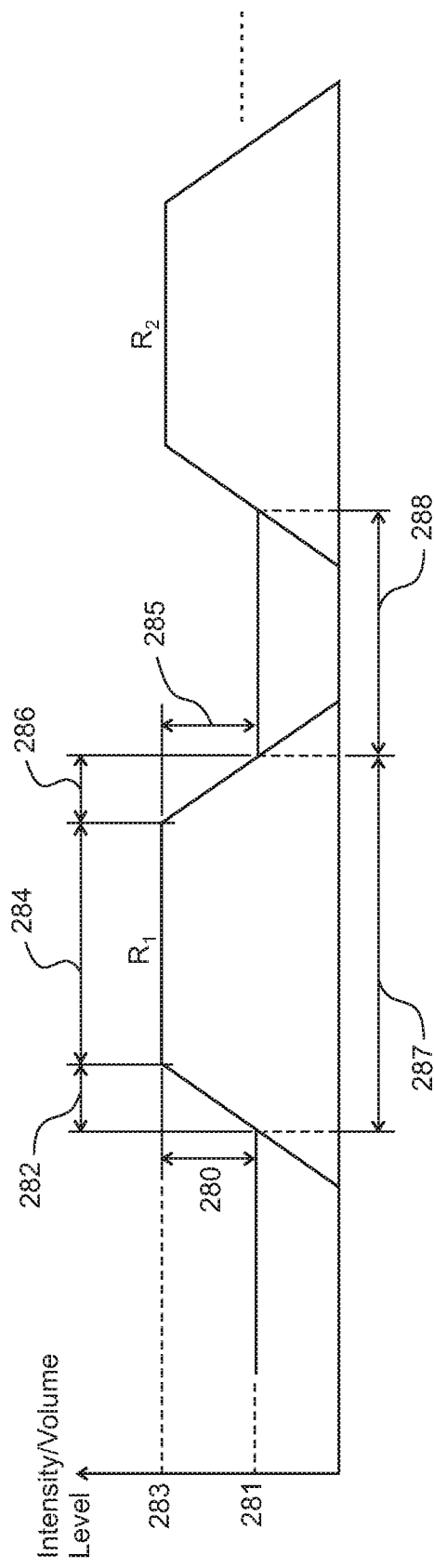
FIG. 13A shows a diagram of a configurable ramping architecture for modulating the intensity of the spatial masking sound in accordance with an embodiment of the invention.

Optionally, the intensity of the masking sound may be modulated according to a ramping profile. For example, a ramp parameter or profile 48 may be set and applied to the masking sound in order to vary the intensity or loudness of the sound over time in accordance with a predetermined profile. FIG. 13A shows a possible periodic ramping architecture with configurable parameters that may be applied to the masking sound to vary its intensity/volume during playback. As shown, the ramping profile may comprise a series of periodically repeating uniform ramps (only two shown at R1, R2). The ramps initiate with a gradual gain 280 relative to the un-ramped original signal level 281 having a rise time period indicated at 282 such that the rate of increase may be adjusted. At the end of the initial gain, the ramp may then be maintained at the upper level 283 for a steady state period indicated at 284 until undertaking a gradual drop in gain back to the un-ramped original signal level 281 as shown at 285 over a fall time period 286 such that the rate of decrease may be adjusted. The overall duration of the ramp is adjustable and shown at 287. The interval time period 288 between the ramps is also adjustable, and there may be no interval in some ramping profiles such that the ramping modulation of the volume of the masking sound is continuous.

Figure 13B:
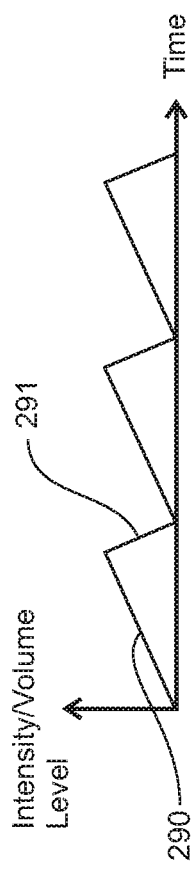
FIG. 13B shows an example of a saw-tooth ramping profile for modulating the intensity of the spatial masking sound in accordance with an embodiment of the invention.

It will be appreciated that all the parameters of the ramping profile outlined above may be adjusted to generate a desired ramping profile to apply to the masking sound to modulate its intensity. By way of example only, FIG. 13B one possible example of a ramping profile is shown in the form of a saw-tooth profile that may be applied to the masking sound to alter its intensity level over time. As shown, the ramping profile has a saw tooth pattern comprising a series of alternating gradual increments and rapid decrements in intensity level. In the saw-tooth profile, there is no interval between the successive ramps. The intensity rise time 290 is long and gradual, and is followed by an intensity drop time 291 that is shorter and abrupt. In this example, there is no steady state period 284 between the intensity increase and decrease periods. The alternating gradual increments and rapid decrements in intensity enhance and maintain a person's attention to sound over time, and this assists the patient to attend to the masking sound in favour of their tinnitus. The ramping profile maintains attention by modulating the sound as a sequence of stimulus ramps, where intensity increases are small and incremental, but stimulus decreases are large and abrupt. It will be appreciated that alternative intensity profiles or patterns may be applied. For example, the pattern may alternatively be in an arc-type as opposed to saw-tooth, or any other periodic or repeating ramping profile.

Generation of Spatial Masking Sound

The next stage 22 after the configuration of the sound processing parameters comprises generating the customised 3D spatial masking sound 54 using audio processing systems (including, for example, onboard audio processing systems in hearing aids and/or headphones) and/or software in accordance with the parameters set in the personalisation step 18 and sound processing step 20. In one embodiment, the synthetic tinnitus sound 15 (which has one or more of its sound attributes matching the corresponding perceived sound attributes of the patient's tinnitus) has its spatial playback properties altered using virtual acoustic sound localisation algorithms and techniques such that it appears to originate from the patient's perceived tinnitus source location during playback over left and right ear-level audio delivery devices. The playback time, diffuse field and any ramping profile are also configured for the masking sound in accordance with the configuration parameters. It will also be appreciated that the 3D spatial making sound 54 generated may be any stimulus sound that is signal processed and modified in accordance with the parameters set in steps 18 and 20. A test playback 56 of the generated masking sound 54 may be played for monitoring with headphones via a programmable attenuator and headphones buffer. If the playback results are favourable at decision point 58, the spatial masking sound is compiled into a digital or electronic sound file 64 or other sound recording for storage on a suitable medium that can be accessed and played by a sound delivery system. In some embodiments, the 3D spatial masking sound is represented in the form of stereo left and right ear audio signals for playback over left and right ear-level audio delivery devices. If the playback results are not favourable, the personalisation and sound processing parameters may be reconfigured as desired, and the masking sound regenerated.

The virtual acoustic technology and examples of hardware systems for generation and/or playback of the spatial masking sound will now be described in more detail.

3. Virtual Acoustic Processing Technology—Sound Localisation

The virtual acoustic technology employed in the tinnitus location diagnosis step 16 and the spatial masking sound generating process step 54 employs the use of sound localisation techniques. Various techniques for altering the perceived location of sound in 3D auditory space are known including using any one or more of the following, in combination or alone, Interaural Time Difference (ITD), Interaural Level Differences (ILD), and Head-Related Transfer Functions (HRTFs). ITD and ILD tend to be used to vary the perceived lateral location of the sound along the midline axis between a person's ears, but HRTFs enable sound to be localised outside of the head and at any desired elevation.

The use of HRTFs is known in audio and sound technology field for creating virtual acoustic spaces. HRTFs describe how a given sound wave (parameterised as frequency and source location) is filtered by the diffraction and reflection properties of the head, pinna, and torso, before the sound reaches the transduction machinery of the ear drum and inner ear. In brief, the HRTF defines how the head and outer ears filter incoming sounds. As is known to those skilled in sound technology, the HRTFs can be measured by placing miniature probe microphones into the patient's ears and recording a bank of impulse responses to broad-band sounds presented to the subject from a range of directions in space.

The impulse responses are sampled in time and a bank of associated HRTFs may be formulated by Fourier transform of the impulse responses. There are two head-related transfer functions, HRTF_L, HRTF_R (one for the left ear and one for the right ear) for each sound direction tested. The HRTFs describe the phase and magnitude response at each ear as a function of frequency, relative to the sound that would received at the centre of the head in the absence of the listener.

The bank of HRTFs for the various sound locations may then be used to generate sounds in specific locations in virtual 3D acoustic space. A spatial sound signal, for example a binaural or stereo audio signal, appearing to originate from a virtual sound source location in 3D auditory space can be created from a monophonic source signal by filtering or convolving that monaural signal with the inverse of the left and right ear HRTFs associated with the desired virtual location. Playing back the binaural audio signals directly into the ears, for example via headphones, creates the illusion of the sound originating from the virtual sound source location.

HRTFs vary from individual to individual and therefore the use of a customised bank of HRTFs measured from the individual patient is beneficial. However, average or ideal HRTFs are known and can be utilised instead of customised HRTFs.

Figure 14:
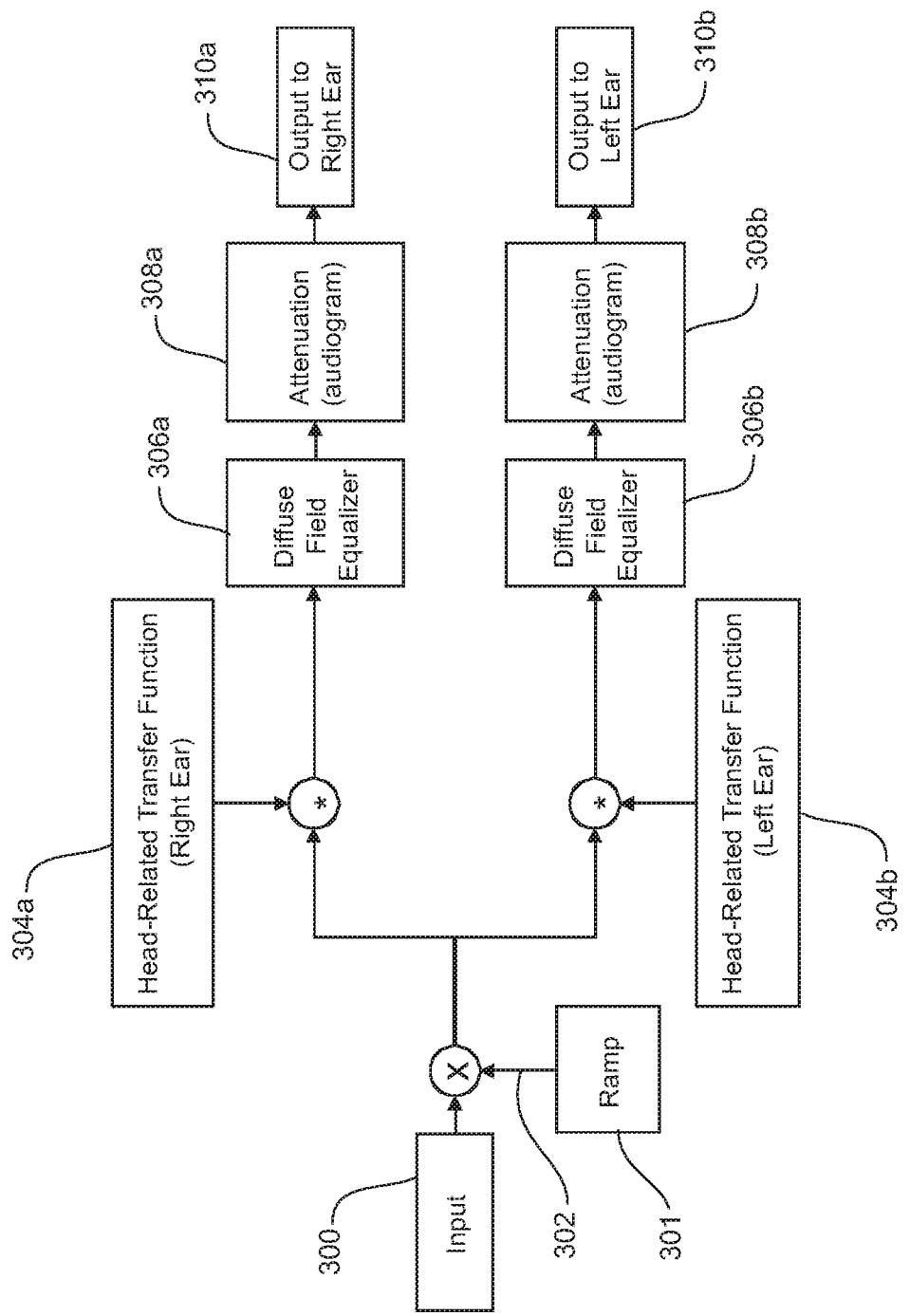
FIG. 14 is a schematic block diagram of a sound processor system for generating a spatial masking sound using virtual acoustic space techniques in accordance with an embodiment of the invention.

Referring to FIG. 14, an example of the virtual acoustic technology hardware setup is shown. The input sound signal, such a monaural signal 300 may have any desired ramp profile applied by a ramp module 301 via modulation with a ramping signal 302, although this is optional. The ramped signal is then filtered through left and right ear impulse responses obtained from the inverse Fourier transforms of the left and right ear HRTFs for the determined tinnitus sound source direction (azimuth and elevation). In other words, the ramped digital input signal is convolved with the inverse Fourier transform of the left and right ear HRTFs at 304a and 304b. The left and right signals may then be filtered through diffuse-field equalisers 306a, 306b and attenuators 308a and 308b if desired. The diffuse field equalisers 306a,306b may be configured based on the parameters set in 46. The diffuse-field may be configured such that the flow of sound energy is substantially equal in all directions from the virtual 3D tinnitus source location or alternatively the diffuse-field may be configured to focus the sound energy in one or more particular directions or regions. The attenuators 308a,308b may be configured based on the audiometer assessment information obtained during the calibration 62. The resulting left 310a and right 310b output signals are then played to the patient via stereo audio devices, such as binaural hearing aids, headphones or earphones or the like.

4. An Example Embodiment of the Hardware Implementation of the Tinnitus Treatment System Various sound delivery systems and devices may be employed to deliver or present the 3D spatial masking sound to the patient. Some possible examples of systems and devices for carrying out this function will now be described by way of example only with reference to FIGS. 15a-20.

4.1 Tinnitus Treatment System Using Hearing Aid Devices Onboard Sound Storage and/or Generation In one embodiment, the sound delivery system for presenting the spatial masking sound to the patient may comprise left and right hearing aids driven by a common external audio controller and which have onboard circuitry for storing and/or generating the spatial masking sound.

Figure 15A:
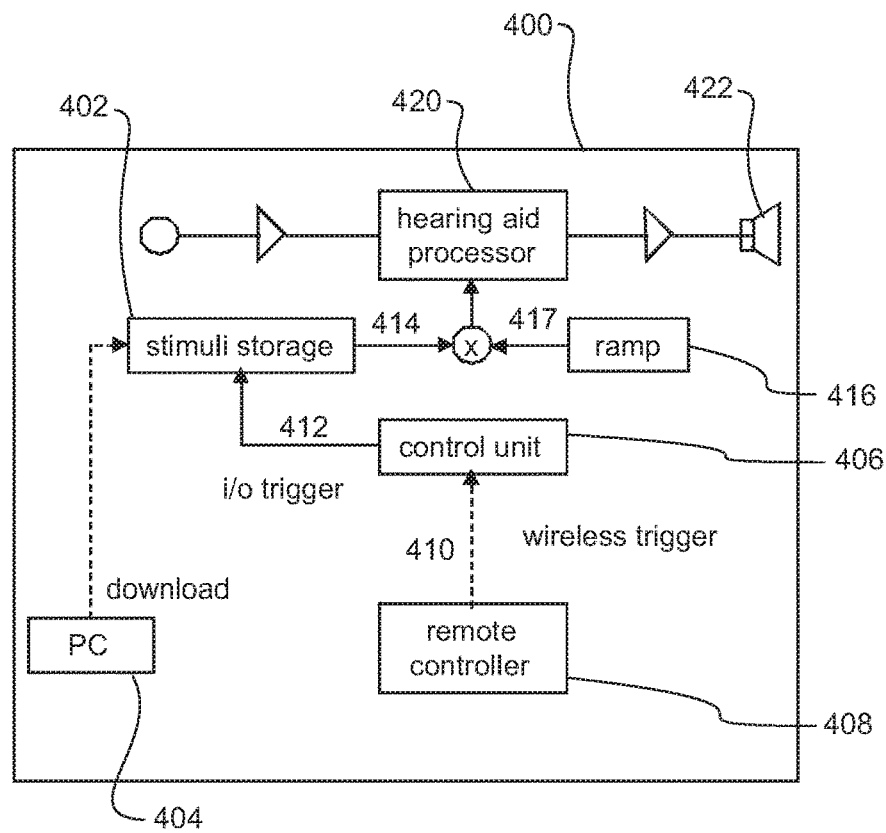
FIG. 15a is a schematic block diagram showing the main modules of a tinnitus treatment system having a first form of hearing aid, having a stored spatial masking signal, that is controlled by a remote control in accordance with an embodiment of the invention.

Referring to FIG. 15a, a first form of hearing aid circuit 400 is shown. In this tinnitus treatment system similar left and right hearing aid circuits are employed although only one is shown for clarity. Each hearing aid circuit comprises a stimuli storage module 402 that is arranged to receive and store the spatial masking sound file, for example uploaded to the hearing aid from an external device such as a personal computer 404 or the like. The hearing aid circuit includes a control unit 406 that communicates with an external remote audio control device 408. In this form of the system, the control unit 406 communicates with the remote control device 408 wirelessly although hardwired connectivity could alternatively be used.

In operation, there is a user interface in the form of a single remote controller 408 which simultaneously communicates with both the left and right hearing aid circuits. The patient may operate the remote controller to initiate playback of the spatial masking sound by sending a trigger signal 410 to each respective control unit. On receiving this trigger signal 410, the control unit 406 is arranged to send a trigger signal 412 to the stimuli storage module 402 that contains the masking sound file and to initiate playback. In this form of the system, the stimuli storage module 402 for the left hearing aid circuit retains the left channel audio signal of the stereo spatial masking sound and the stimuli storage module of the right hearing aid circuit retains the right channel audio signal.

In this embodiment, a ramp unit or module 416 in each hearing aid circuit is configurable to apply a ramping profile to the spatial masking sound signal via a ramping signal 417 to modulate the intensity or loudness of the playback in accordance with a desired ramping profile, as previously explained. It will be appreciated that the ramp unit 416 may be deactivated if no ramping modulation is to be applied.

In their respective circuits, the left and right audio signals 414 after being multiplied by any desired ramping signal 417 are received by the hearing aid processor 420 of the circuit where they are buffered and amplified, and transmitted to the hearing aid speaker 422 for playback of the audio sound into the patient's left and right ears respectively.

The left and right hearing aid circuits are synchronised such that the playback of their respective left and right audio signals, representing the spatial masking sound, creates playback of the masking sound so as to appear to originate from a virtual sound source location that substantially corresponds to the tinnitus source sound location as perceived by the patient.

Figure 15B:
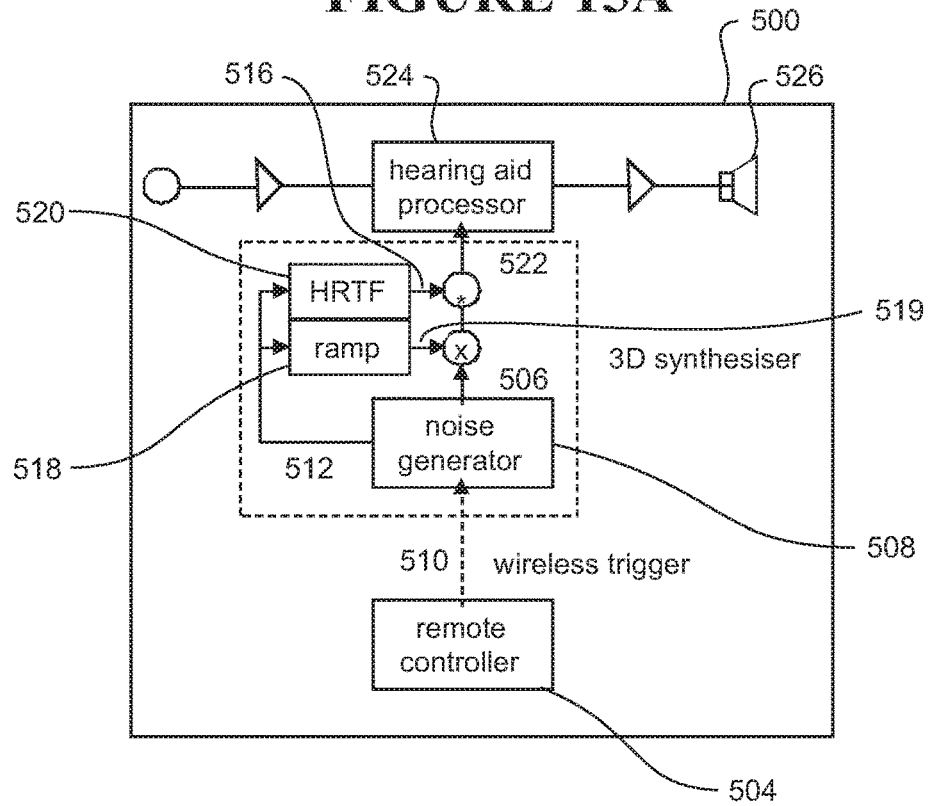
FIG. 15b is a schematic block diagram showing the main modules of a tinnitus treatment system having a second form of hearing aid that generates a spatial masking signal and that is controlled by a remote control in accordance with an embodiment of the invention.

Referring to FIG. 15*b*, a second form of hearing aid circuit that may be employed in a tinnitus treatment system comprising left and right hearing aids synchronously controlled by a remote controller is shown. In contrast to the first form hearing circuit that stores the respective left and right audio signals of the spatial masking sound onboard for playback, the second form hearing aid circuit 500 comprises an onboard sound processor, such as a 3D synthesiser 502, that is arranged to generate the left and right audio signals in real-time for delivering to the patient.

As with the first preferred form of hearing aid circuit, a single remote controller 504 is arranged to communicate with each of the left and right hearing aid circuit and control the synchronised generation of the left and right audio signals representing the spatial masking sound. For example, the remote controller is arranged to send trigger signals 510, via wireless or wired connection, to the 3D synthesiser circuits 502 of each respective hearing aid circuit. In response to this trigger, a noise generator 508 generates a monaural masking sound 506 that is then subjected to sound processing to create the spatial and other sound attribute properties required of the masking sound when ultimately delivered by the left and right hearing aid circuit.

By way of example, the monaural sound signal generated by the noise generator 506 may be selected from a range of stimuli, including white noise, music, tones, background noise, sound effects or the like. On the initiation of the monaural sound signal generation, a simultaneous trigger signal 512 is sent to initiate ramp 519 and HRTF 516 signals that are arranged to modify the monaural signal 506. In particular, a ramp module 518 generates the ramp signal 519 that modulates the monaural signal 506 in accordance with a desired ramping profile. The HRTF module 520 for each circuit is arranged to generate an HRTF impulse response signal 516 that is convolved with the ramped monaural signal so as to generate the spatial property for the respective left and right audio signals such that when delivered to the patient they combine to present a masking sound that appears to originate from a virtual sound source location substantially corresponding to the 3D spatial location as perceived by the patient. As before, the ramp module 518 may be deactivated if no ramping of the masking sound is required.

The modified left and right signals 522 (from each of the left and right hearing aid circuits) then together represent the spatial masking sound. The hearing aid processor 524 of each circuit is again used to amplify and buffer the respective modified left and right signals for sending to the speaker 526 of each hearing aid so as to deliver the sound to the patient. In an alternative form, the 3D synthesizer may be implemented or incorporated in the hearing aid processor 524

Figure 16:
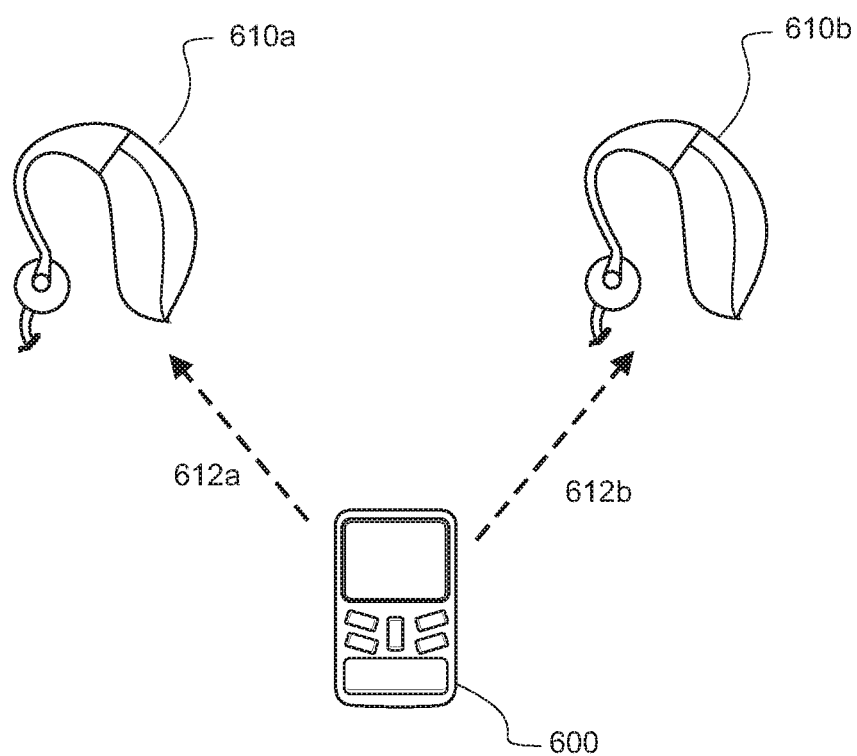
FIG. 16 is a schematic diagram showing the hardware devices of a tinnitus treatment system employing synchronised left and right hearing aids controlled by a remote control in accordance with FIGS. 15A and 15B.

FIG. 16 shows the hardware devices of the tinnitus treatment system that may be employed to implement either forms of the hearing aid circuits described with reference to FIGS. 15A and 15B. By way of example, left 610*a* and right 610*b* hearing aids for a patient to wear are shown. The playback of the spatial masking signal via the hearing aids is controlled synchronously by an external remote controller 600 that sends the hearing aids respective control signals 612*a*, 612*b* wirelessly, for example using Near Field Magnetic Induction (NFMI), Bluetooth, FM, infrared, or any other wireless transmission. The remote controller may alternatively be hardwired via cable(s) to the hearing aids if desired.

External Sound Storage and/or Generation

In another embodiment, the sound delivery system for presenting the spatial masking sound to the patient may comprise conventional left and right hearing aids driven by a common external audio control device that is arranged to store, generate, and/or send the left and right audio signals representing the spatial masking sound to the hearing aids for playback.

Figure 17:
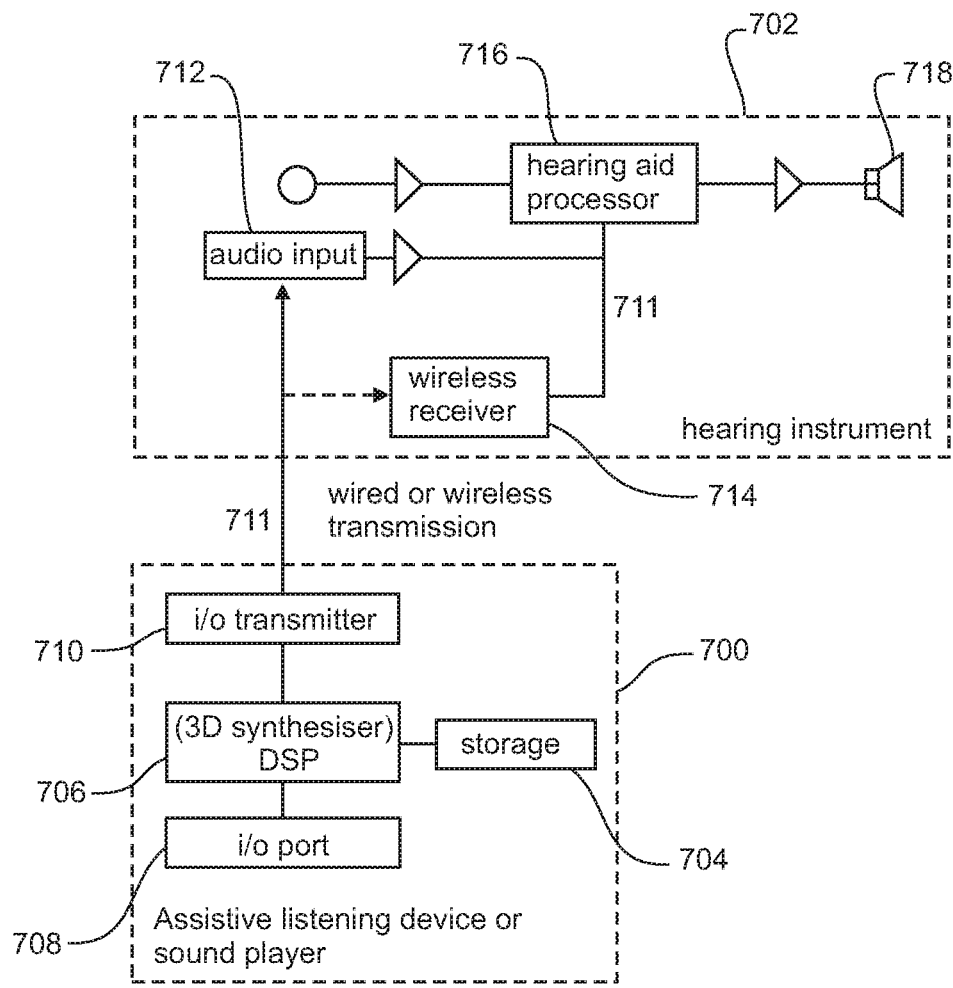
FIG. 17 is a schematic block diagram showing the main modules of a tinnitus treatment system having a hearing aid that is controlled by an external audio control device that is configured to generate the spatial masking signal for the hearing aid.

Referring to FIG. 17, this embodiment of the tinnitus treatment system comprises an external audio control device 700 that is arranged to send left and right audio signals to respective left and right hearing aid circuits 702 (only one shown for clarity) for playback. In one form, the audio control device 702 may comprise a storage memory module 704 for storing the spatial masking sound and/or stimuli sounds for generating the spatial masking sound. Such stimuli sounds may include sounds that are configured to match one or more of the patient's perceived tinnitus sound attributes. A sound processor module 706, such as a 3D synthesiser, is provided for generating the left and right audio signals representing the spatial masking sound using virtual acoustic space processing in real-time of the stimuli sounds from memory 704. The 3D synthesiser may operate in a similar manner to that described with reference to the 3D synthesiser of FIG. 15*b* by altering the spatial properties of the stimuli sounds to create a virtual sound source location that corresponds to that of the perceived tinnitus source location. The sound processor module 706 may be provided in the form of a programmable hardware device, such as a Digital Signal Processor (DSP) or any other programmable microprocessor. In addition to implementing a 3D synthesiser function to generate the real-time spatial masking sound, the sound processor module may also be arranged as an audio player. The audio player may be provided with a user interface that is operable to control delivery (e.g. playback) of the masking sound, such as start, stop and pause functions, and other typical audio parameters such as volume.

The audio player of the sound processor module 706 can be configured to control generation of the masking sound by the 3D synthesiser and presentation/delivery of the sound to the audio delivery devices, and/or can be configured to load and control playback of masking sound audio files that have been preloaded or stored in storage memory module 704 or which are received via the input/output port 708 explained below. In other embodiments, the sound processor module 706 need not necessarily include a 3D synthesizer for generating masking sounds and could be arranged only as an audio player that controls playback of stored masking sound files in memory 704 or received from the input/output port 708.

An input/output port 708 is provided for receiving sound files and for controlling the sound processing parameters and configurations to generate the desired spatial masking sound for playback. A user interface may also be provided for controlling the generation and playback of the spatial masking sound. The user interface may be integrated with the audio control device 700 or an external device that communicates with the control device via the input/output port 708. The user interface may be provided in the form of any suitable electronic user interface, including, but not limited to, buttons, dials, switches, touch-screen or any combination thereof. An input/output transmission module 710 is provided to enable wireless or wired connectivity and communication with each of the left and right hearing aid devices.

When playback of the spatial masking sound is initiated by a user operating the audio control device 700, the left and right audio signals 711 generated by the 3D synthesiser and/or provided from the storage module 704 are simultaneously and synchronously sent to the respective audio input modules 712 of the respective hearing aid circuits (if hardwired to the audio control device) or to the respective wireless receiver modules 714 if wireless communication is employed. The audio signals 711 are then received and processed by their respective hearing aid processors 716, for example they may be buffered and amplified, and then sent to the respective left and right hearing aid speakers 718 for playback to the user.

Figure 18:
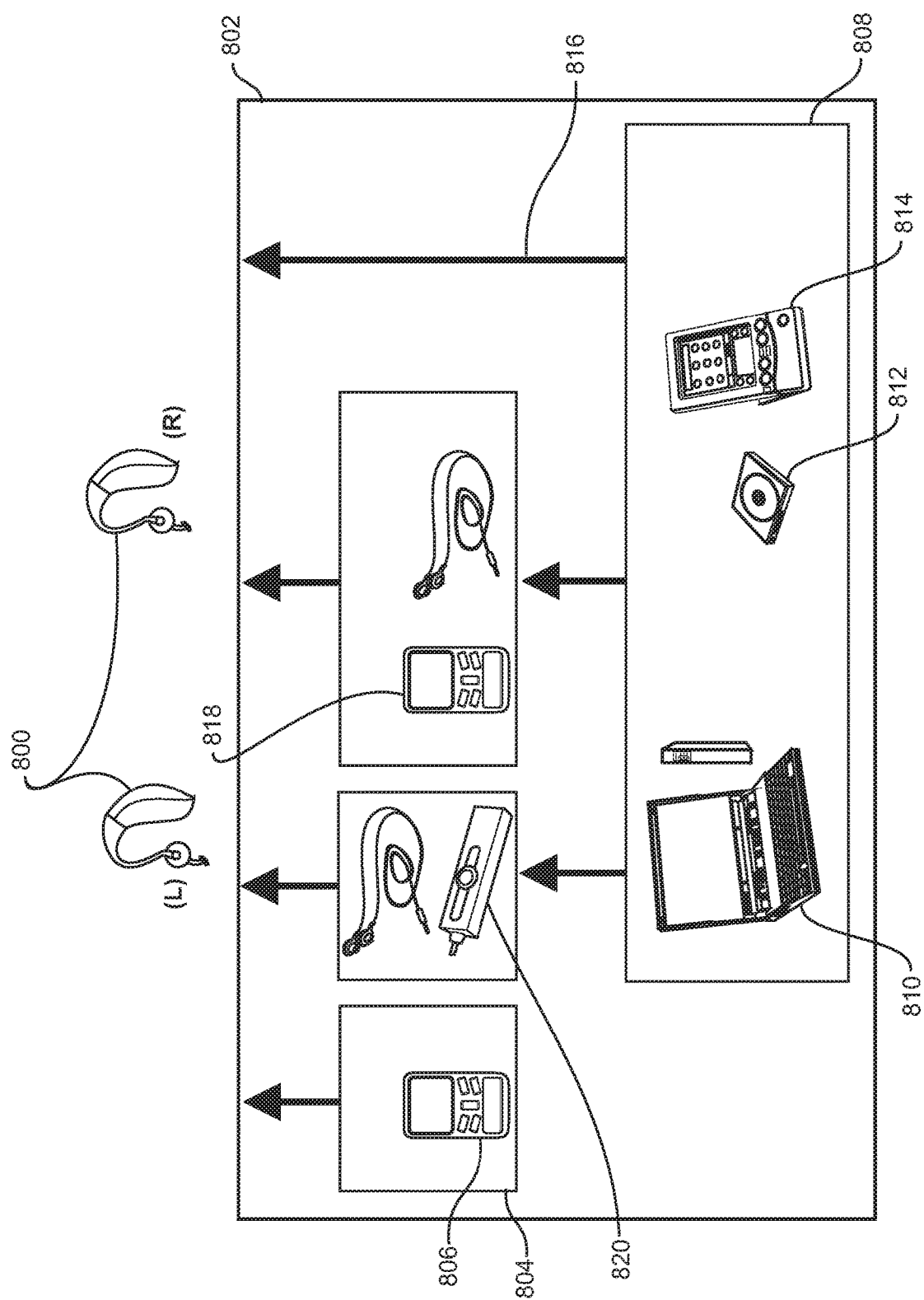
FIG. 18 is a schematic diagram showing examples of various hardware devices that can be employed to implement the tinnitus treatment system shown in FIG. 17, and in particular employing synchronised left and right hearing aids that can be driven by a range of different audio control devices.
Figure 19:
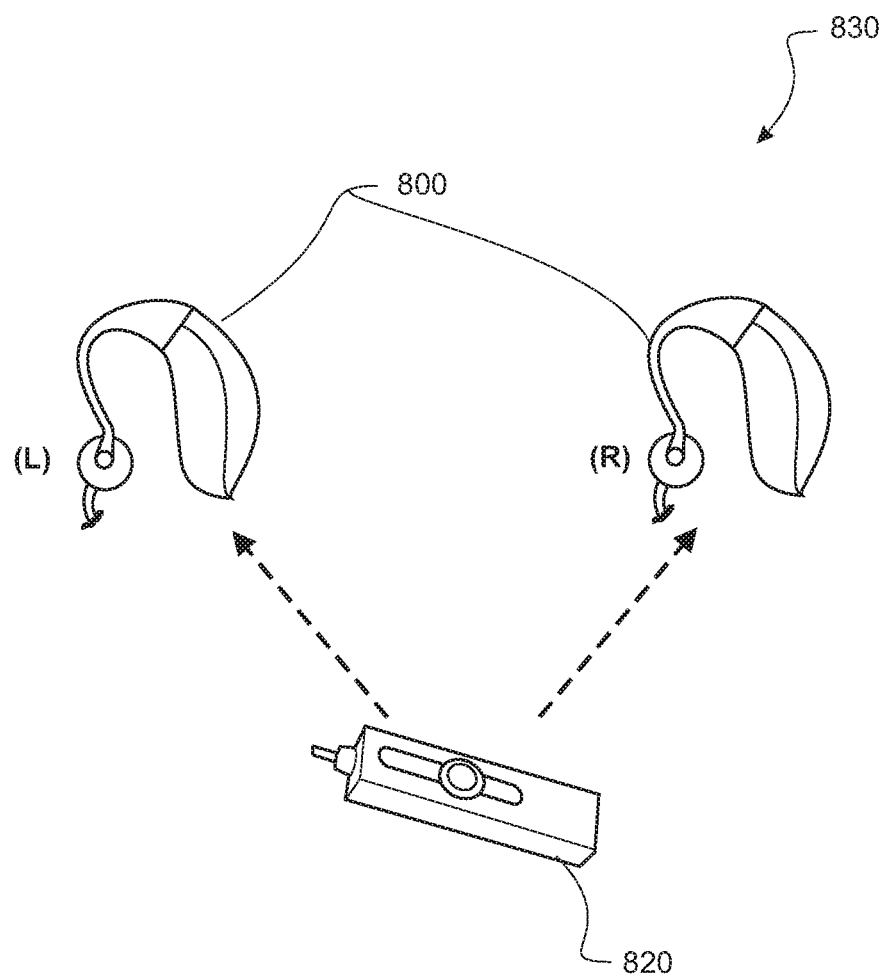
FIG. 19 is a schematic diagram showing the hardware devices that can be employed to implement the tinnitus treatment system shown in FIG. 17, and in particular employing left and right hearing aids that are synchronously driven by an external audio control device.

FIGS. 18 and 19 show a range of various hardware devices that may be employed to implement the tinnitus treatment system of FIG. 17. As mentioned the system comprises left and right audio delivery devices in the form of left and right hearing aids that are controlled by an audio control device or devices 802. The audio control device may be provided in various forms with varying capabilities. For example, in some forms the audio control device may simply store, transmit and control playback of the spatial masking sound, but in other forms the audio control device may have sound processing capabilities such that it is also operable to generate and modify the spatial masking sound. It will also be appreciated that these functions may be spread over multiple interconnected or communicating devices.

In one form 804, the masking sound is stored on a remote device 806 that transmits and controls playback over the hearing aid devices 800.

In another form 808, the audio control device may comprise any suitable generic sound or audio player or device having such functionality, such as a Personal Computer 810, portable audio player 812, PDA 814 or the like, that is arranged to generate, store and/or control playback of the spatial masking sound. The audio player may send the left and right audio signals representing the spatial masking sound directly to the hearing aids 816 or indirectly via other intermediate transmission or control devices. For example, such intermediate control devices may comprise a remote control device 818 or wireless transmission device 820. It will be appreciated that connection and communication between the audio player and any intermediate control devices may be wirelessly, for example using NFMI, Bluetooth, FM, infrared or any other wireless communication protocol, or via wired cables, or a combination of the two.

In another form 830, the audio control device 820 may be in the form a wireless transmission device that is arranged to store, transmit and control playback of the spatial masking sound via wireless communication with the hearing aids 800. In this form, the spatial masking signal may be uploaded onto the audio control device 820 in the form of a digital sound file for playback via an onboard audio player that can process the sound file and generate the audio signals for transmission to the hearing aid devices 800.

4.2 Tinnitus Treatment System Using Headphones

Figure 20:
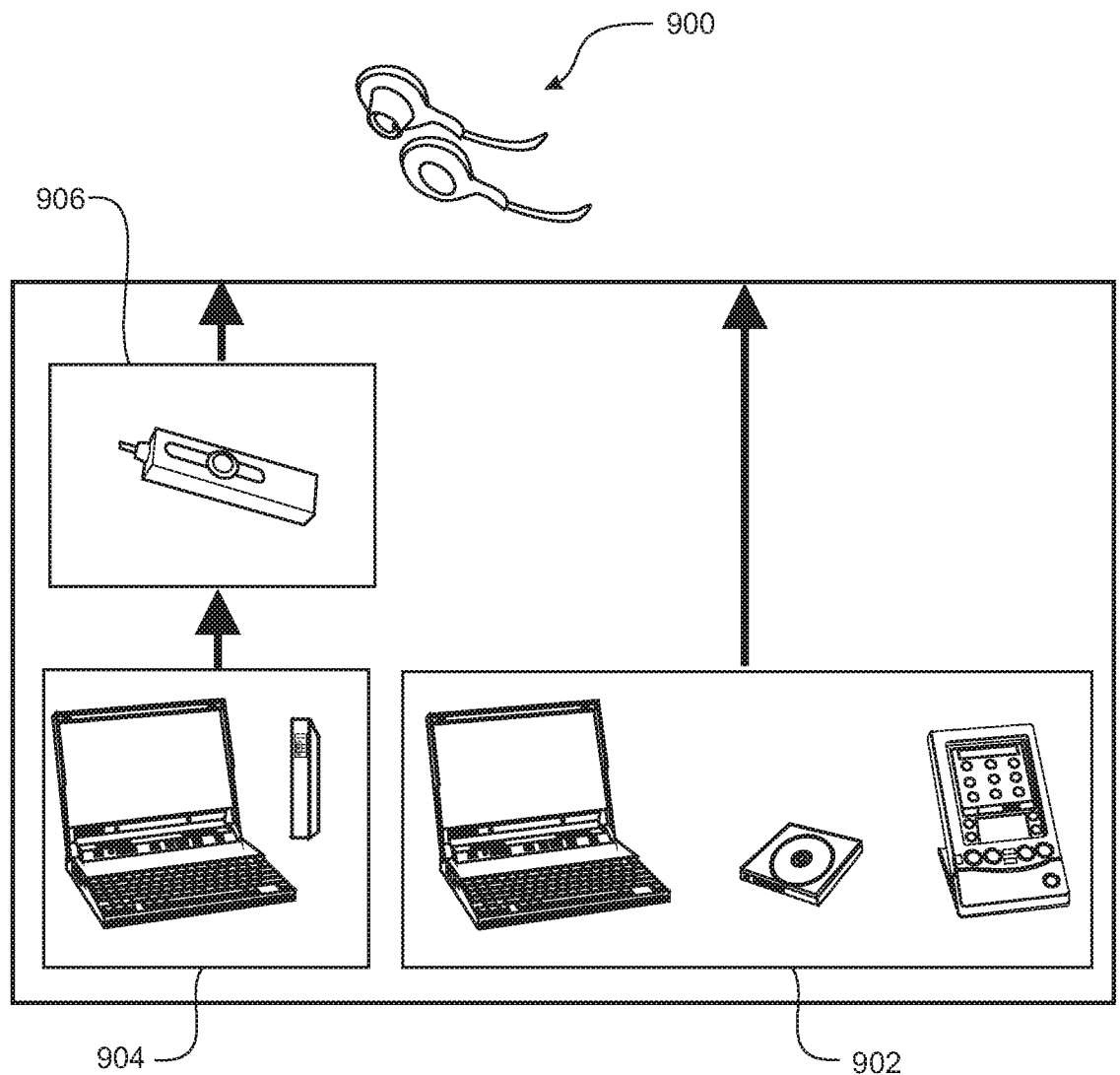
FIG. 20 shows a schematic diagram of hardware implementation of tinnitus treatment system of another embodiment of the invention that employs left and right stereo headphones that may be driven by various audio control devices.

In another embodiment shown in FIG. 20, the sound delivery system may comprise audio delivery devices in the form of standard left and right headphones 900, ear buds or earphones that are worn by the user and from which the left and right audio signals representing the spatial masking sound is played.

It will be appreciated that the audio signals may be transmitted to the headphones 900 from any suitable audio control device that is capable of storing, generating and/or controlling playback of the spatial masking sound. For example, the audio control device 902 may be in the form of a Personal Computer, portable audio player, PDA, cell phone or any other suitable device. Wireless headphones may alternatively be used and in which case a wireless transmission device 906 integrated or external to the audio control device 904 may be employed to transmit the audio signals to the headphones for playback.

4.3 Tinnitus Treatment System—Integrated or Standalone Sound Delivery System

In other embodiments, the sound delivery system may comprise left and right audio delivery devices that are integrated with one or more onboard audio control devices rather than having an external audio control device. The onboard audio control device may store the masking sound file for playback or generate the masking sound in real-time, and is operable via a user interface to control synchronised playback of the left and right audio signals over their respective left and right audio delivery devices to generate the audible spatial masking sound for the patient. In one form, the sound delivery system may be a standalone treatment system. In another form the sound delivery system may be integrated into another device or expand the functionality of another device. For example, the sound delivery system may be integrated into twin left and right hearing aid system with onboard audio control for the spatial masking sound playback. The left and right hearing aids may communicate wirelessly to coordinate synchronised playback of the left and right audio signals representing the spatial masking sound.

In summary various sound delivery system embodiments are possible and the audio control device may be completely or partially integrated with the audio delivery devices or entirely separate and external.

The foregoing description of the invention includes preferred forms thereof. Modifications may be made thereto without departing from the scope of the invention as defined by the accompanying claims.

The invention claimed is:

1. An electronic system for determining a spatial property of a source of tinnitus as perceived by a person comprising:
   an electronic sound generation system comprising an audio player that is operable to present digital test sounds to the person from a range of virtual sound source locations in 3D auditory space;
   an electronic feedback system that is arranged to receive input data representing person feedback indicative of the virtual sound source location that most closely corresponds to a spatial location in 3D auditory space of the source of the tinnitus as perceived by the person; and output spatial information indicative of the spatial location of the source of the tinnitus based on the person's feedback, wherein the spatial information comprises data indicative of a 3D direction vector representing a direction in 3D auditory space corresponding to a spatial location of the source of the tinnitus as perceived by the person; and a graphical user interface presented on a display of or connected to the system, the graphical user interface being operable to control one or more functions of the electronic sound generation system and the electronic feedback system.

2. The electronic system according to claim 1, wherein the electronic sound generation system is configured to sequentially present digital test sounds to the person from a range of different virtual sound source locations.

3. The electronic system according to claim 1, wherein the electronic sound generation system is user operable via the graphical user interface to present the digital test sounds from user selected virtual sound source locations.

4. The electronic system according to claim 1, wherein the digital test sound has one or more sound attributes that substantially correspond or match one or more perceived sound attributes of the person's tinnitus.

5. The electronic system according to claim 4, wherein the sound attributes comprise any one or more of the following: pitch, frequency, bandwidth, temporal properties, intensity, loudness, and sound type.

6. The electronic system according to claim 1, wherein the electronic sound generation system is operable to present the digital test sound to the person sequentially at different azimuth and elevation angles within respective predetermined azimuth and elevation ranges relative to a reference point in a 3D auditory space reference frame.

7. The electronic system according to claim 6, wherein the reference point is at the centre of a midline axis between the ears.

8. The electronic system according to claim 6, wherein the electronic sound generation system is operable to present the digital test sounds by continuously sweeping through the entire azimuth and elevation ranges.

9. The electronic system according to claim 6, wherein the electronic sound generation system is configured to present the test sounds sequentially at a series of discrete azimuth and elevation angles.

10. The electronic system according to claim 1, wherein the graphical user interface of the system is operable by the person as a self-assessment tool.

11. The electronic system according to claim 1, wherein the spatial information further comprises a magnitude corresponding to the spatial location of the source of the tinnitus as perceived by the person.

12. A method of determining a spatial property of a source of tinnitus as perceived by a person, the method being performed on an electronic system comprising:

an electronic sound generation system comprising an audio player that is operable to present digital test sounds from a range of virtual sound source locations in 3D auditory space;

an electronic feedback system that is operable to:
receive input data representing person feedback indicative of the virtual sound source location that most closely corresponds to a spatial location in 3D auditory space of the source of the tinnitus as perceived by the person; and output spatial information indicative of the spatial location of the source of the tinnitus based on the person's feedback, wherein the spatial information comprises data indicative of a 3D direction vector representing a direction in 3D auditory space corresponding to a spatial location of the source of the tinnitus as perceived by the person; and a graphical user interface presented on a display of or connected to the system that is operable to control one or more functions of the electronic sound generation system and the electronic feedback system, wherein the method comprises the steps of:

sequentially presenting digital test sounds to the person from a series of virtual sound source locations in 3D auditory space via the audio player of the electronic sound generation system;

receiving feedback, via the graphical user interface, from the person as to virtual sound source location that most closely corresponds to a spatial location in 3D auditory space of the source of the tinnitus as perceived by the person; and outputting from the electronic feedback system the virtual sound source location as data indicative of a 3D direction vector representing a direction in 3D auditory space corresponding to a spatial location of the source of the tinnitus as perceived by the person.

13. The method of claim 12, wherein outputting the virtual sound source location further comprises data indicative of a magnitude representing a distance in 3D auditory space corresponding to the spatial location of the source of the tinnitus as perceived by the person.

* * * * *